(12) United States Patent
Petersen

(10) Patent No.: US 8,021,392 B2
(45) Date of Patent: Sep. 20, 2011

(54) METHODS AND SURGICAL KITS FOR MINIMALLY-INVASIVE FACET JOINT FUSION

(75) Inventor: David A. Petersen, Clearwater, FL (US)

(73) Assignee: minSURG International, Inc., Clearwater, FL (US)

( * ) Notice: Subject to any disclaimer, the term of this patent is extended or adjusted under 35 U.S.C. 154(b) by 40 days.

(21) Appl. No.: 12/238,255

(22) Filed: Sep. 25, 2008

(65) Prior Publication Data

US 2009/0076551 A1 Mar. 19, 2009

Related U.S. Application Data

(63) Continuation-in-part of application No. 11/232,519, filed on Sep. 22, 2005, now Pat. No. 7,708,761, which is a continuation-in-part of application No. 10/992,720, filed on Nov. 22, 2004, now abandoned.

(51) Int. Cl.
*A61B 17/70* (2006.01)

(52) U.S. Cl. ...................................................... 606/247

(58) Field of Classification Search .... 623/17.11–17.16; 606/246–249, 86 R, 90, 250–279
See application file for complete search history.

(56) References Cited

U.S. PATENT DOCUMENTS

| | | | | |
|---|---|---|---|---|
| 3,848,601 A | * | 11/1974 | Ma et al. | ...................... 606/86 A |
| 4,344,190 A | | 8/1982 | Lee et al. | |
| 4,501,269 A | * | 2/1985 | Bagby | ............................ 606/279 |
| 4,545,374 A | | 10/1985 | Jacobson | |
| 4,654,314 A | | 3/1987 | Takagi et al. | |
| 4,736,738 A | * | 4/1988 | Lipovsek et al. | ................ 606/88 |
| 4,737,411 A | | 4/1988 | Graves, Jr. et al. | |
| 4,834,757 A | * | 5/1989 | Brantigan | ................... 623/17.11 |
| 4,877,020 A | | 10/1989 | Vich | |
| 4,878,915 A | * | 11/1989 | Brantigan | ................... 623/17.11 |
| 4,961,740 A | * | 10/1990 | Ray et al. | ....................... 606/247 |

(Continued)

FOREIGN PATENT DOCUMENTS

RU 2204342 C2 5/2003

(Continued)

OTHER PUBLICATIONS

*Orthopedic Development Corp. v. Nufix Inc.*, Plaintiff's Motion for a Preliminary Injunction, Oct. 15, 2008.

(Continued)

*Primary Examiner* — Alvin J. Stewart
(74) *Attorney, Agent, or Firm* — Don J. Pelto; Sheppard, Mullin, Richter & Hampton LLP

(57) ABSTRACT

Disclosed herein are methods and surgical kits that can be used to fuse facet joints via a minimally invasive procedure (including an arthroscopic or percutaneous procedure). An exemplary method includes creating an incision; locating a facet joint with a distal end of a pin; sliding a substantially hollow drill guide over said pin wherein said drill guide comprises a proximal end, a distal end; removing said pin from within said drill guide; inserting a drill bit into said drill guide; drilling a hole into a bone of said facet joint; removing said drill bit; inserting a facet joint bone plug into said hole using a bone plug inserter having a raised portion at or near is proximal end, wherein said raised portion prevents over-insertion of said bone plug; and removing said drill guide.

24 Claims, 14 Drawing Sheets

U.S. PATENT DOCUMENTS

| | | | |
|---|---|---|---|
| 4,990,161 A | 2/1991 | Kampner | |
| 5,009,666 A | 4/1991 | Van Syckle et al. | |
| 5,015,247 A * | 5/1991 | Michelson | 606/247 |
| 5,026,373 A | 6/1991 | Ray et al. | |
| 5,152,791 A | 10/1992 | Hakamatsuka et al. | |
| 5,298,254 A | 3/1994 | Prewett et al. | |
| 5,425,772 A | 6/1995 | Brantigan | |
| 5,439,464 A | 8/1995 | Shapiro | |
| 5,443,514 A * | 8/1995 | Steffee | 128/898 |
| 5,445,639 A | 8/1995 | Kuslich et al. | |
| 5,489,307 A * | 2/1996 | Kuslich et al. | 128/898 |
| 5,505,732 A | 4/1996 | Michelson | |
| 5,527,312 A * | 6/1996 | Ray | 606/301 |
| D374,283 S * | 10/1996 | Michelson | D24/135 |
| 5,591,235 A * | 1/1997 | Kuslich | 606/261 |
| 5,593,409 A | 1/1997 | Michelson | |
| 5,645,598 A * | 7/1997 | Brosnahan, III | 623/17.11 |
| 5,683,391 A * | 11/1997 | Boyd | 606/264 |
| 5,700,291 A * | 12/1997 | Kuslich et al. | 606/96 |
| 5,709,683 A | 1/1998 | Bagby | |
| 5,720,748 A | 2/1998 | Kuslich et al. | |
| 5,769,897 A | 6/1998 | Harle | |
| 5,772,661 A * | 6/1998 | Michelson | 606/86 A |
| 5,782,919 A * | 7/1998 | Zdeblick et al. | 623/17.16 |
| D397,436 S | 8/1998 | Michelson | |
| 5,797,909 A * | 8/1998 | Michelson | 606/914 |
| 5,803,904 A * | 9/1998 | Mehdizadeh | 600/235 |
| 5,865,847 A | 2/1999 | Kohrs et al. | |
| 5,885,299 A * | 3/1999 | Winslow et al. | 606/99 |
| 5,888,224 A * | 3/1999 | Beckers et al. | 623/17.16 |
| 5,895,427 A * | 4/1999 | Kuslich et al. | 128/898 |
| 5,899,908 A * | 5/1999 | Kuslich et al. | 606/96 |
| 5,906,616 A | 5/1999 | Pavlov et al. | |
| 5,928,242 A | 7/1999 | Kuslich et al. | |
| D412,435 S | 8/1999 | Cultice | |
| 5,968,098 A | 10/1999 | Winslow | |
| 6,004,326 A * | 12/1999 | Castro et al. | 606/99 |
| 6,033,419 A | 3/2000 | Hamblin et al. | |
| 6,039,762 A | 3/2000 | McKay | |
| 6,042,582 A | 3/2000 | Ray | |
| 6,045,580 A | 4/2000 | Scarborough et al. | |
| D424,421 S | 5/2000 | Ono | |
| 6,063,088 A * | 5/2000 | Winslow | 606/86 A |
| RE36,758 E | 6/2000 | Fitz | |
| 6,080,155 A | 6/2000 | Michelson | |
| 6,080,158 A * | 6/2000 | Lin | 606/247 |
| 6,083,225 A * | 7/2000 | Winslow et al. | 606/86 A |
| 6,086,595 A * | 7/2000 | Yonemura et al. | 606/99 |
| 6,113,602 A * | 9/2000 | Sand | 606/86 A |
| 6,139,551 A * | 10/2000 | Michelson et al. | 606/79 |
| 6,143,033 A | 11/2000 | Paul et al. | |
| 6,146,420 A * | 11/2000 | McKay | 623/17.16 |
| 6,149,651 A | 11/2000 | Dewry et al. | |
| 6,158,437 A | 12/2000 | Vagley | |
| 6,200,322 B1 * | 3/2001 | Branch et al. | 606/96 |
| 6,210,412 B1 | 4/2001 | Michelson | |
| 6,224,630 B1 | 5/2001 | Bao et al. | |
| 6,228,111 B1 | 5/2001 | Tormala et al. | |
| 6,241,770 B1 | 6/2001 | Michelson | |
| 6,241,771 B1 | 6/2001 | Gresser et al. | |
| 6,258,125 B1 | 7/2001 | Paul et al. | |
| 6,261,586 B1 | 7/2001 | McKay | |
| 6,264,656 B1 | 7/2001 | Michelson | |
| 6,264,657 B1 * | 7/2001 | Urbahns et al. | 606/914 |
| 6,264,677 B1 | 7/2001 | Simon et al. | |
| 6,267,763 B1 | 7/2001 | Castro | |
| 6,270,528 B1 | 8/2001 | Mckay | |
| 6,283,966 B1 * | 9/2001 | Houfburg | 606/914 |
| 6,302,913 B1 | 10/2001 | Ripamonti et al. | |
| 6,315,795 B1 | 11/2001 | Scarborough et al. | |
| 6,346,123 B1 | 2/2002 | McKay | |
| 6,371,986 B1 | 4/2002 | Bagby | |
| 6,371,988 B1 | 4/2002 | Pafford et al. | |
| 6,371,989 B1 | 4/2002 | Chauvin et al. | |
| 6,375,655 B1 | 4/2002 | Zdeblick et al. | |
| 6,383,221 B1 | 5/2002 | Scarborough | |
| 6,395,035 B2 | 5/2002 | Bresina et al. | |
| 6,398,811 B1 | 6/2002 | McKay | |
| 6,409,765 B1 | 6/2002 | Bianchi et al. | |
| 6,432,436 B1 | 8/2002 | Gertzman et al. | |
| 6,436,098 B1 | 8/2002 | Michelson | |
| 6,440,444 B2 | 8/2002 | Boyce et al. | |
| 6,443,987 B1 | 9/2002 | Bryan | |
| 6,452,586 B1 | 9/2002 | Holmdahl et al. | |
| 6,485,518 B1 * | 11/2002 | Cornwall et al. | 623/17.11 |
| 6,491,724 B1 | 12/2002 | Ferree | |
| 6,494,883 B1 | 12/2002 | Ferree | |
| 6,500,205 B1 | 12/2002 | Michelson | |
| 6,500,206 B1 | 12/2002 | Bryan | |
| 6,511,509 B1 | 1/2003 | Ford et al. | |
| 6,520,907 B1 | 2/2003 | Foley et al. | |
| 6,520,967 B1 * | 2/2003 | Cauthen | 606/99 |
| 6,524,312 B2 * | 2/2003 | Landry et al. | 606/86 A |
| 6,537,320 B1 | 3/2003 | Michelson | |
| 6,544,289 B2 | 4/2003 | Wolfinbarger, Jr. et al. | |
| 6,548,569 B1 | 4/2003 | Williams et al. | |
| 6,551,995 B1 | 4/2003 | Oppermann et al. | |
| 6,554,863 B2 | 4/2003 | Paul et al. | |
| 6,565,574 B2 * | 5/2003 | Michelson | 606/90 |
| 6,582,431 B1 | 6/2003 | Ray | |
| 6,585,770 B1 | 7/2003 | White et al. | |
| 6,585,772 B2 | 7/2003 | Hunter et al. | |
| 6,610,065 B1 * | 8/2003 | Branch et al. | 606/84 |
| 6,613,091 B1 | 9/2003 | Zdeblick et al. | |
| 6,626,945 B2 | 9/2003 | Simon et al. | |
| 6,632,246 B1 | 10/2003 | Simon et al. | |
| 6,632,247 B2 | 10/2003 | Boyer, II et al. | |
| 6,638,309 B2 | 10/2003 | Bonutti | |
| 6,641,613 B2 | 11/2003 | Sennett | |
| 6,645,206 B1 | 11/2003 | Zdeblick | |
| 6,648,893 B2 | 11/2003 | Dudasik | |
| 6,652,584 B2 | 11/2003 | Michelson | |
| 6,652,586 B2 | 11/2003 | Hunter et al. | |
| 6,652,592 B1 | 11/2003 | Grooms et al. | |
| 6,669,729 B2 | 12/2003 | Chin | |
| D484,785 S | 1/2004 | Plumer | |
| 6,689,167 B2 | 2/2004 | Bagby | |
| 6,695,851 B2 | 2/2004 | Zdeblick et al. | |
| 6,695,882 B2 | 2/2004 | Bianchi et al. | |
| 6,696,073 B2 | 2/2004 | Boyce et al. | |
| 6,702,856 B2 | 3/2004 | Bonutti | |
| 6,709,458 B2 | 3/2004 | Michelson | |
| 6,719,795 B1 | 4/2004 | Cornwall et al. | |
| 6,743,255 B2 | 6/2004 | Ferree | |
| 6,747,121 B2 | 6/2004 | Gogolewski | |
| 6,758,849 B1 | 7/2004 | Michelson | |
| 6,770,074 B2 | 8/2004 | Michelson | |
| 6,790,233 B2 | 9/2004 | Brodke et al. | |
| 6,793,679 B2 | 9/2004 | Michelson | |
| 6,814,756 B1 | 11/2004 | Michelson | |
| 6,827,740 B1 | 12/2004 | Michelson | |
| 6,838,493 B2 | 1/2005 | Williams et al. | |
| 6,840,961 B2 | 1/2005 | Tofighi et al. | |
| 6,843,807 B1 | 1/2005 | Boyce et al. | |
| 6,852,125 B2 | 2/2005 | Simon et al. | |
| 6,867,247 B2 | 3/2005 | Williams et al. | |
| 6,893,462 B2 | 5/2005 | Buskirk et al. | |
| 6,902,578 B1 | 6/2005 | Anderson et al. | |
| 6,905,517 B2 | 6/2005 | Bonutti | |
| 6,923,810 B1 | 8/2005 | Michelson | |
| 6,929,647 B2 | 8/2005 | Cohen | |
| 6,972,035 B2 | 12/2005 | Michelson | |
| 6,986,788 B2 | 1/2006 | Paul et al. | |
| 6,989,029 B2 | 1/2006 | Bonutti | |
| 6,991,654 B2 * | 1/2006 | Foley | 623/17.16 |
| 7,001,385 B2 | 2/2006 | Bonutti | |
| 7,008,453 B1 | 3/2006 | Michelson | |
| 7,012,034 B2 | 3/2006 | Heide et al. | |
| 7,018,414 B2 | 3/2006 | Brau et al. | |
| 7,033,392 B2 | 4/2006 | Schmiel et al. | |
| D521,858 S | 5/2006 | Roy | |
| 7,044,968 B1 | 5/2006 | Yaccarino, III et al. | |
| 7,048,762 B1 | 5/2006 | Sander et al. | |
| 7,056,342 B2 | 6/2006 | Michelson | |
| 7,060,096 B1 | 6/2006 | Schopf et al. | |
| 7,077,866 B2 | 7/2006 | Gresser et al. | |
| 7,087,082 B2 | 8/2006 | Paul et al. | |

| | | |
|---|---|---|
| 7,087,540 B2 | 8/2006 | Heide et al. |
| 7,101,398 B2 | 9/2006 | Dooris et al. |
| 7,105,023 B2 | 9/2006 | Eckman |
| 7,118,598 B2 | 10/2006 | Michelson |
| 7,223,269 B2 * | 5/2007 | Chappuis .................... 606/86 R |
| 7,241,313 B2 | 7/2007 | Unwin et al. |
| 7,244,258 B2 | 7/2007 | Burkus et al. |
| 7,264,634 B2 | 9/2007 | Schmieding |
| 7,273,498 B2 | 9/2007 | Bianchi et al. |
| 7,300,440 B2 | 11/2007 | Zdeblick et al. |
| D556,905 S | 12/2007 | Barry |
| 7,320,688 B2 * | 1/2008 | Foley et al. .................... 606/99 |
| D566,277 S * | 4/2008 | Barry .......................... D24/155 |
| 7,371,238 B2 | 5/2008 | Soboleski et al. |
| 7,396,360 B2 | 7/2008 | Lieberman |
| 7,396,365 B2 | 7/2008 | Michelson |
| 7,399,303 B2 | 7/2008 | Michelson |
| D574,495 S * | 8/2008 | Petersen ...................... D24/140 |
| 7,452,369 B2 * | 11/2008 | Barry .......................... 606/279 |
| 7,491,205 B1 | 2/2009 | Michelson |
| 7,517,358 B2 * | 4/2009 | Petersen ...................... 606/247 |
| 7,569,054 B2 | 8/2009 | Michelson |
| 7,637,913 B2 | 12/2009 | De Villiers et al. |
| 7,678,149 B2 | 3/2010 | Bianchi |
| 7,699,878 B2 | 4/2010 | Pavlov et al. |
| 7,708,761 B2 * | 5/2010 | Petersen ...................... 606/247 |
| 2001/0020186 A1 | 9/2001 | Boyce et al. |
| 2001/0039388 A1 | 11/2001 | Korotko et al. |
| 2002/0077641 A1 | 6/2002 | Michelson |
| 2002/0111680 A1 | 8/2002 | Michelson |
| 2003/0004530 A1 * | 1/2003 | Reo .............................. 606/185 |
| 2003/0009235 A1 | 1/2003 | Manrique et al. |
| 2003/0028251 A1 | 2/2003 | Mathews |
| 2003/0149438 A1 * | 8/2003 | Nichols et al. .................. 606/99 |
| 2004/0097929 A1 * | 5/2004 | Branch et al. ................... 606/61 |
| 2004/0106997 A1 | 6/2004 | Lieberson |
| 2004/0106999 A1 | 6/2004 | Mathews |
| 2004/0138748 A1 | 7/2004 | Boyer, II et al. |
| 2004/0215344 A1 | 10/2004 | Horchschuler et al. |
| 2004/0230303 A1 | 11/2004 | Gomes et al. |
| 2005/0004672 A1 | 1/2005 | Pafford et al. |
| 2005/0015150 A1 | 1/2005 | Lee |
| 2005/0049705 A1 | 3/2005 | Hale et al. |
| 2005/0124993 A1 | 6/2005 | Chappuis |
| 2005/0131538 A1 | 6/2005 | Chervitz et al. |
| 2005/0149021 A1 | 7/2005 | Tozzi |
| 2005/0149030 A1 | 7/2005 | Serhan et al. |
| 2005/0159746 A1 | 7/2005 | Grob et al. |
| 2005/0165483 A1 | 7/2005 | Ray, III et al. |
| 2005/0177240 A1 | 8/2005 | Blain |
| 2005/0197700 A1 | 9/2005 | Boehm et al. |
| 2005/0222687 A1 | 10/2005 | Vunjak-Novakovic et al. |
| 2005/0261682 A1 | 11/2005 | Ferree |
| 2005/0267482 A1 * | 12/2005 | Hyde, Jr. ........................ 606/79 |
| 2005/0267578 A1 | 12/2005 | Michelson |
| 2005/0288672 A1 | 12/2005 | Ferree |
| 2006/0036243 A1 * | 2/2006 | Sasso et al. .................... 606/61 |
| 2006/0041311 A1 * | 2/2006 | McLeer ...................... 623/17.11 |
| 2006/0064099 A1 * | 3/2006 | Pavlov et al. ................... 606/72 |
| 2006/0085068 A1 * | 4/2006 | Barry ......................... 623/17.11 |
| 2006/0106381 A1 | 5/2006 | Ferree et al. |
| 2006/0111779 A1 * | 5/2006 | Petersen .................... 623/17.11 |
| 2006/0116688 A1 | 6/2006 | Boyd et al. |
| 2006/0125814 A1 * | 6/2006 | Asai et al. ...................... 345/204 |
| 2006/0149254 A1 | 7/2006 | Lauryssen et al. |
| 2006/0173543 A1 | 8/2006 | Brau et al. |
| 2006/0247632 A1 | 11/2006 | Winslow et al. |
| 2006/0276790 A1 * | 12/2006 | Dawson et al. ................. 606/61 |
| 2007/0282220 A1 * | 12/2007 | Abernathie .................... 600/564 |
| 2008/0015701 A1 | 1/2008 | Garcia et al. |
| 2008/0177310 A1 | 7/2008 | Reiley |
| 2008/0234758 A1 * | 9/2008 | Fisher et al. .................. 606/309 |
| 2008/0275505 A1 | 11/2008 | Yuan et al. |
| 2008/0287996 A1 | 11/2008 | Soboleski et al. |
| 2009/0024166 A1 | 1/2009 | Carl et al. |
| 2009/0024219 A1 | 1/2009 | McLeer |
| 2009/0030459 A1 * | 1/2009 | Hoy et al. ...................... 606/247 |
| 2009/0030461 A1 | 1/2009 | Hoy et al. |
| 2009/0036926 A1 | 2/2009 | Hestad |
| 2009/0036927 A1 * | 2/2009 | Vestgaarden ................. 606/247 |
| 2009/0036986 A1 | 2/2009 | Lancial et al. |
| 2009/0125066 A1 * | 5/2009 | Kraus et al. ................... 606/279 |
| 2009/0131986 A1 * | 5/2009 | Lee et al. ...................... 606/247 |
| 2009/0157119 A1 * | 6/2009 | Hale .............................. 606/247 |
| 2009/0182377 A1 * | 7/2009 | Petersen ....................... 606/247 |
| 2009/0216274 A1 * | 8/2009 | Morancy-Meister et al. 606/247 |
| 2010/0114166 A1 * | 5/2010 | Kohm et al. .................. 606/247 |
| 2010/0137910 A1 * | 6/2010 | Cawley et al. ................ 606/247 |

FOREIGN PATENT DOCUMENTS

| | | |
|---|---|---|
| RU | 2302837 C1 | 7/2007 |
| WO | 0062684 | 10/2000 |
| WO | 0141681 | 6/2001 |

OTHER PUBLICATIONS

*Orthopedic Development Corp.* v. *Nufix Inc.*, Complaint, filed Oct. 15, 2008.
*Orthopedic Development Corp.* v. *Nufix Inc.*, Order of Dismissal, Jan. 14, 2009.
*Orthopedic Development Corp.* v. *Nutech Medical*, Complaint, filed Feb. 7, 2008.
*Orthopedic Development Corp.* v. *Nutech Medical*, Counterclaim Defendants' Motion to Dismiss, Mar. 26, 2008.
*Orthopedic Development Corp.* v. *Nutech Medical*, Amended Answer and Counterclaim of Defendants, Apr. 14, 2008.
*Orthopedic Development Corp.* v. *Nutech fvledical*, Order of Dismissal, Nov. 4, 2008.
Powers et al, Minimally invasive fusion and fixation techniques, Jun. 4, 2006, Elsevier Saunders, Neurosurg Clin N AM 17, pp. 477-489.
Stein, M., et al., Percutaneous Facet Joint Fusion: Preliminary Experience, J.Vasc. Interv. Radiol., Jan.-Feb. 1993, 4(1), pp. 69-74.
Youn-Kwan et al, Facet fusion in the lumbosacral spine: A 2-year follow-up study, Jul. 2002, Neurosurgery 51, No. 1, www.neurosurgery-online.com, pp. 88-96.
Craig, J. Bone Joint Surg. Am. 38:93-102 (1956).
Branch et al., Principles and Techniques in Spine Surgery/Lumbar Interbody Fusion: "Posterior Lumbar Interbody Fusion: The Keystone Technique", Aspen Publishers, Inc. Surg. Neurol. 17: 211-219 (1989).
Jaikumar et al., Neurosurgery 51[Suppl 2]:1-14 (2002).
Kambin, The Journal of Arthroscopic and Related Surgery 8(3):287-295 (1992).
Khoo et al., Neurosurgery 51[Suppl 2]:166-181 (2002).
Scoliosis and Other Spinal Deformities: "Idiopathic Scoliosis", W.B. Saunders Company, pp. 106-130 (1978).
Lieberman et al., SPINE 26(14):1631-1638 (2001).
Moe, Southern Medical Journal 50:67-81 (1957).
Peters et al., Neurosurgery 51[Suppl 2]:96-103 (2002).
Polly et al., SPINE 30(16S):S44-S51 (2005).
Stein et al., Journal of Vascular and Interventional Radiology 4:69-74 (1993).
Vamvanij et al., Journal of Spinal Disorder 11(5):375-382 (1998).
*Frontier Devices, Inc.* v. *minSURG Corporation, Inc.*, Court Order to Transfer the Case, Sep. 30, 2010.
*Frontier Devices, Inc.* v. *minSURG Corporation, Inc.*, Plaintiff's Motion for Leave to File Second Amended Complaint, Aug. 13, 2010.
*minSURG Corporation, Inc.* v. *Nuvasive, Inc. et al.*, Bacterin International, Inc.'s Opposition to Plaintiff's Motion for Preliminary Injunction, Sep. 1, 2010.
*VG Innovations, Inc.* v. *minSURG Corporation, Inc.*, Memo in Opposition to Motion for Preliminary Injunction, Sep. 1, 2010.
*minSURG International, Inc.* v. *Nuvasive, Inc. et al.*, Declaration of J. Thomas Vitt. in Opposition to Plaintiff's Motion for Preliminary Injunction, Sep. 1, 2010.
*minSURG International, Inc.* v. *Nuvasive, Inc. et al.*, Declaration of Dr. David Clark Lee in Opposition to Plaintiff's Motion for Preliminary Injunction, Sep. 1, 2010.
*minSURG International, Inc.* v. *Nuvasive, Inc. et al.*, Defendants' Joint Opposition to Plaintiff's Motion for Preliminary Injunction, Sep. 1, 2010.

*minSURG International, Inc.* v. *Nuvasive, Inc. et al.*, Exhibit 1 to Exhibit 2, Sep. 1, 2010.
*minSURG International, Inc.* v. *Nuvasive, Inc. et al.*, Exhibit 2, Affidavit of James B. Macon, MD., Sep. 1, 2010.
*minSURG International, Inc.* v. *Nuvasive, Inc. et al.*, Exhibit 1 to Exhibit 2 (James B. Macon, MD. Curriculum Vitae) Sep. 1, 2010.
*minSURG International, Inc.* v. *Nuvasive, Inc. et al.*, Defendant Facet Fusion, LLC's Opposition to Plaintiff's Motion for Preliminary Injunction, Sep. 1, 2010.
*minSURG International, Inc.* v. *Nuvasive, Inc. et al.*, Answer, Affirmative Defenses and Counterclaims by Defendant Facet Fusion Technologies, LLC. Sep. 2, 2010.
*minSURG International, Inc.* v. *Nuvasive, Inc. et al.*, Frontier Devices, Inc.'s Supplemental Memorandum in Opposition to Plaintiff's Motion for Preliminary Injunction, Sep. 1, 2010.
*minSURG International, Inc.* v. *Nuvasive, Inc. et al.*, Declaration of Harold B. Childs in Support of Defendants' Opposition to Plaintiff's Motion for a Preliminary Injunction, Sep. 1, 2010.
*minSURG International, Inc.* v. *Nuvasive, Inc. et al.*, Declaration of James E. Hansen in Support of Defendant Facet Fusion LLC's Opposition to Plaintiff's Motion for Preliminary Injunction, Sep. 1, 2010.
*minSURG International, Inc.* v. *Nuvasive, Inc. et al.*, Declaration of Kirk Cannon in Support of Defendants' Opposition to Plaintiff's Motion for a Preliminary Injunction, Sep. 1, 2010.
*minSURG International, Inc.* v. *Nuvasive, Inc. et al.*, Declaration of Mike Reilly in Opposition to Plaintiff's Motion for Preliminary Injunction, Sep. 1, 2010.
*minSURG International, Inc.* v. *Nuvasive, Inc. et al.*, Notice of Filing Declaration in Support of Defendants' Opposition to Plaintiff's Motion for a Preliminary Injunction, Sep. 1, 2010.
*minSURG International, Inc.* v. *Nuvasive, Inc. et al.*, Nutech Medical, Inc., Nufix, Inc., and Kenneth Horton's Response and Memorandum in Opposition to Plaintiff's Motion for Preliminary Injunction, Sep. 1, 2010.
*minSURG International, Inc.* v. *Nuvasive, Inc. et al.*, Osteotech, Inc.'s Memorandum in Opposition to Plaintiff's Motion for Preliminary Injunction, Sep. 1, 2010.
*minSURG International, Inc.* v. *Nuvasive, Inc. et al.*, Plaintiff's Brief in Support of Motion to Dismiss the Counterclaim of Defendant Bacterin International, Inc., Sep. 8, 2010.
*minSURG International, Inc.* v. *Nuvasive, Inc. et al.*, Defendant Bacterin's Opposition to Plaintiff's Motion to Dismiss, Sep. 22, 2010.
*minSURG International, Inc.* v. *Nuvasive, Inc. et al.*, Plaintiff's Brief in Support of Motion to Dismiss the First, Third and Fourth Counterclaims of Defendant Facet Fusion Technologies, LLC, Sep. 27, 2010.
*minSURG International, Inc.* v. *Nuvasive, Inc. et al.*, Defendant VG Innovations, Inc.'s Request for Judicial Notice, Oct. 1, 2010.
*Nufix, Inc.* v. *minSURG International, Inc. et al.*, Court Order to Transfer the Case, Oct. 1, 2010.
*Frontier Devices, Inc.* v. *minSURG Corporation, Inc.*, Complaint, Jul. 2, 2010.
*Frontier Devices, Inc.* v. *minSURG Corporation, Inc.*, Amended Complaint, Jul. 27, 2010.
*Frontier Devices, Inc.* v. *minSURG Corporation, Inc.*, Memorandum in Support of Motion to Dismiss, Jul. 29, 2010.
*minSURG International, Inc.* v. *Nuvasive, Inc. et al.*, Complaint, Jul. 19, 2010.
*minSURG International, Inc.* v. *Nuvasive, Inc. et al.*, Exhibits to Complaint (patents), Jul. 19, 2010.
*minSURG International, Inc.* v. *Nuvasive, Inc. et al.*, Brief in Support of Motion for Preliminary Injunction, Aug. 3, 2010.
*VG Innovations, Inc.* v. *minSURG Corporation, Inc.*, Complaint, Jul. 6, 2010.
*VG Innovations, Inc.* v. *minSURG Corporation, Inc.*, Notice of Removal, Aug. 3, 2010.
*NuFix, Inc.* v. *minSURG Corporation, Inc.*, Complaint, Jun. 29, 2010.
*NuFix, Inc.* v. *minSURG Corporation, Inc.*, Exhibits (patents), Jun. 29, 2010.
*NuFix, Inc.* v. *minSURG Corporation, Inc.*, Memorandum in Support of Motion to Dismiss, Jul. 22, 2010.

\* cited by examiner

METHODS AND SURGICAL KITS FOR MINIMALLY-INVASIVE FACET JOINT FUSION

PRIOR APPLICATIONS

This application is a continuation-in-part of U.S. patent application Ser. No. 11/232,519 filed Sep. 22, 2005 now U.S. Pat. No. 7,708,761 which is a continuation-in-part of U.S. patent application Ser. No. 10/992,720, filed Nov. 22, 2004 now abandoned.

FIELD OF THE INVENTION

The present invention relates to methods and surgical kits that can be used to fuse facet joints through minimally invasive procedures.

BACKGROUND OF THE INVENTION

In the United States, about 10% of the population will suffer from back pain sometime in the next year. This occurrence is more than any other injury or disease except for the common cold and flu. About one-third of those suffering from back pain will not recover and will live with persistent, disabling symptoms. These numbers are cumulative year after year.

One root cause of back pain, particularly the persistent and disabling kind, is problems (including arthritis) with facet joints. The back of each vertebra has two sets of facet joints. One pair faces upward and the other pair faces downward. Within each set there is a facet joint on the left side of each vertebra and a facet joint on the right side of each vertebra.

Facet joints are the system of joints that allow movement (forward bending, backward bending and twisting) of the spine. While these joints allow movement of the spine, their interlocking nature also helps to stabilize the spine.

Similar to other joints in the body, each facet joint is surrounded by a capsule of connective tissue and produces synovial fluid to nourish and lubricate the joint. The joint surfaces themselves are coated with a thick spongy material called articular cartilage that enables the bones of each joint to smoothly move against the other.

Osteoarthritis is probably the most common cause of facet joint pain. This degenerative disease causes progressive cartilage deterioration. Without the spongy cartilaginous cushion, joint bones begin to rub against each other when at rest and during movement causing a substantial amount of pain. Therefore, one option to treat this type of pain is to join rubbing portions of bone together so that this painful friction does not occur.

Present surgical solutions available for facet joint dysfunctions are high-risk, complex and invasive pedicle screw or compression screw based operations associated with prolonged recovery times (such as from about 6 to 24 months; see, for example, U.S. Pat. Nos. 6,485,518 and 6,648,893. The high risk nature of these surgeries leads to uncertain clinical outcomes which can motivate doctors and patients to choose non-surgical symptomatic treatments. While these treatments can help to alleviate back pain temporarily, the underlying cause of the pain continues to progressively worsen. Moreover, there are additional problems associated with screw-based approaches to facet joint fusion. For example, screw-type fixations can work their way loose over time, negating any beneficial effect of the original procedure.

Thus, there is room for great improvement in the surgical treatment of facet joint dysfunction.

SUMMARY OF THE INVENTION

The present invention provides a minimally-invasive procedure and associated surgical tools that can be used to fuse facet joint bones without the use of a screw-based approach. Instead of relying on a screw to hold rubbing facet joints together, the present invention drills a hole into the facet joint and inserts a bone plug into the created hole. The bone plug allows natural bone in-growth into and around the plug such that a strong and permanent fusion results. The present invention may be so minimally-invasive that, in some embodiments, it can be practiced arthroscopically or percutaneously. Moreover, in many instances, the procedure can be out-patient.

Specifically, one embodiment according to the present invention includes a method comprising: creating an incision; locating a facet joint with a distal end of a pin wherein the facet joint is formed between two opposing bones and the pin includes a distal end and a proximal end; inserting a spatula; sliding a substantially hollow drill guide over the spatula/pin wherein the drill guide includes a proximal end, a distal end, a handle and a marking wherein the handle is nearer to the proximal end of the drill guide than to the distal end and wherein the distal end includes opposed teeth that can be inserted into the facet joint and wherein the marking indicates the rotational orientation of the two opposed teeth; removing the pin from within the drill guide; inserting a drill bit into the drill guide; drilling a hole into a bone of the facet joint; removing the drill bit; inserting a facet joint bone plug into the hole; and removing the drill guide. In some embodiments, there are two opposed teeth. In some embodiments, the hole is drilled in a manner that permits some of the drilled bone to remain in the drilled hole.

Another embodiment according to the present invention includes a method comprising creating an incision; locating a facet joint with a distal end of a pin wherein the facet joint is formed between two opposing bones and the pin includes a distal end and a proximal end; sliding a substantially hollow spatula over the pin wherein the spatula includes a proximal end, a distal end and a body wherein the distal end includes a planar wedge and the body includes a marking that can indicate the orientation of the planar wedge; adjusting the rotation of the planar wedge until the planar wedge enters the facet joint; sliding a substantially hollow drill guide over the spatula wherein the drill guide includes a proximal end, a distal end, a handle and a marking wherein the handle is nearer to the proximal end of the drill guide than to the distal end, wherein the distal end includes two opposed teeth that can be inserted into the facet joint and the marking indicates the rotational orientation of the two opposed teeth and wherein when the marking on the drill guide is matched or aligned with the marking on the spatula, the orientation of the two opposed teeth is in approximately the same plane defined by the planar wedge; aligning the markings on the spatula and the drill guide; removing the spatula from within the drill guide; inserting a drill bit into the drill guide; drilling a hole into a bone of the facet joint; removing the drill bit; inserting a facet joint bone plug into the hole; removing the drill guide; and closing the incision wherein the pin has also been removed prior to the closing of the incision.

In other embodiments according to the present invention, the inserting of the facet joint bone plug into the hole includes sliding an inserter instrument into the drill guide wherein the inserter instrument has a proximal end and a distal end and a facet joint bone plug associated with the distal end; and disengaging the facet joint bone plug from the distal end of the inserter instrument into the drilled hole.

A particular embodiment according to the present invention includes a method comprising creating an incision; locating a facet joint with a spinal pin; accessing the facet joint with a substantially hollow spatula wherein the spatula includes a proximal end, a distal end, a body and a marking on the body wherein the distal end includes a planar wedge and the accessing includes sliding the substantially hollow spatula over the spinal pin while adjusting the rotation of the planar wedge until the planar wedge enters the facet joint; sliding a substantially hollow drill guide over the spatula wherein the drill guide includes a proximal end, a distal end, a handle and a marking wherein the handle is nearer to the proximal end of the drill guide than to the distal end and wherein the distal end includes two opposed teeth and wherein when the marking on the drill guide is matched or aligned with the marking on the spatula, the orientation of the opposed teeth is in approximately the same plane defined by the planar wedge; matching or aligning the markings on the spatula and the drill guide; removing the spinal pin and the spatula from within the drill guide; inserting a drill bit into the drill guide; drilling a hole into a bone of the facet joint; removing the drill bit; sliding an inserter instrument into the drill guide wherein the inserter instrument has a proximal end and a distal end and a facet joint bone plug associated with the distal end; disengaging the facet joint bone plug from the distal end of the inserter instrument into the drilled hole; and removing the drill guide. In some embodiments, the drilling includes grinding the bone and compacting some of the drilled bone within said hole.

In particular embodiments according to the present invention, the above described methods can further comprise confirming the location of the pin at the facet joint. In one embodiment, the confirming is accomplished with at least one x-ray.

In another embodiment according to the present invention, the method further includes tapping the spatula further into the facet joint following the initial inserting of the planar wedge into the facet joint.

In another embodiment according to the present invention, the method further includes tapping the drill guide following the aligning of the markings so that the opposed teeth of the drill guide engage facet joint bone to secure the orientation of the drill guide until the removing of the drill guide.

In another embodiment according to the present invention, the method further includes tapping the facet joint bone plug into the facet joint following the inserting.

In other embodiments, the present invention includes a method including creating an incision; locating a facet joint with a distal end of a pin wherein the facet joint is formed between two opposing bones and the pin includes the distal end and a proximal end; sliding a substantially hollow drill guide over the pin wherein the drill guide includes a proximal end, a distal end, and a handle wherein the handle is nearer to the proximal end of the drill guide than to the distal end, the distal end includes opposed teeth that can be inserted into the facet joint and; removing the pin from within the drill guide; inserting a drill bit into the drill guide; drilling a hole into a bone of the facet joint; removing the drill bit; inserting a facet joint bone plug into the hole using a bone plug inserter having a raised portion at or near is proximal end, wherein the raised portion prevents over-insertion of the bone plug; and removing the drill guide. In some embodiments, the distal end of the drill guide includes two opposed teeth. In other embodiments, the distal end of the drill guide includes a plurality of teeth, wherein the plurality of teeth includes two opposed teeth and one or more smaller teeth disposed between the two opposed teeth. In some embodiments, the method also includes confirming the location of the pin at the facet joint, for example by taking at least one x-ray. In certain embodiments, the drill guide includes a marking that indicates the rotational orientation of the opposed teeth. In some embodiments, the drilling includes grinding the bone and compacting some of the drilled bone within the hole.

In certain embodiments, the present invention includes a method including: creating an incision; locating a facet joint with a distal end of a pin wherein the facet joint is formed between two opposing bones and the pin includes the distal end and a proximal end; sliding a substantially hollow spatula over the pin wherein the spatula includes a proximal end, a distal end and a body wherein the distal end includes a planar wedge; adjusting the rotation of the planar wedge until the planar wedge enters the facet joint; sliding a substantially hollow drill guide over the spatula wherein the drill guide includes a proximal end, a distal end, and a handle wherein the handle is nearer to the proximal end of the drill guide than to the distal end, the distal end includes opposed teeth that can be inserted into the facet joint; removing the spatula from within the drill guide; inserting a drill bit into the drill guide; drilling a hole into a bone of the facet joint; removing the drill bit; inserting a facet joint bone plug into the hole using a bone plug inserter having a raised portion at or near its proximal end, wherein the raised portion prevents over-insertion of the bone plug; removing the drill guide; and closing the incision wherein the pin has also been removed prior to the closing of the incision. In particular embodiments, the distal end of the drill guide includes two opposed teeth. In certain embodiments, the distal end of the drill guide includes a plurality of teeth, wherein the plurality of teeth includes two opposed teeth and one or more smaller teeth disposed between the two opposed teeth. In some embodiments, the method also includes confirming the location of the pin at the facet joint, including by taking at least one x-ray. In particular embodiments, the body of the spatula includes a marking that can indicate the orientation of the planar wedge. In other embodiments, the spatula further includes a marking and wherein when the marking on the drill guide is matched or aligned with the marking on the spatula, the orientation of the opposed teeth is in approximately the same plane defined by the planar wedge. In some embodiments, the method also includes the step of aligning the markings on the spatula and the drill guide. In some embodiments, the step of inserting the facet joint bone plug into the hole includes sliding an inserter instrument into the drill guide wherein the inserter instrument has a proximal end and a distal end and a facet joint bone plug associated with the distal end; and disengaging the facet joint bone plug from the distal end of the inserter instrument into the drilled hole. In some embodiments, the method also includes tapping the spatula further into the facet joint following the initial inserting of the planar wedge into the facet joint. In some embodiments, the method also includes tapping the drill guide following the aligning of the markings so that the opposed teeth of the drill guide engage facet joint bone to secure the orientation of the drill guide until the removing of the drill guide. In some embodiments, the method also includes tapping the facet joint bone plug into the facet joint following the inserting. In some embodiments, the drilling includes grinding the bone and compacting some of the drilled bone within the hole.

In other embodiments, the present invention includes a method including: creating an incision; locating a facet joint with a spinal pin; accessing the facet joint with a substantially hollow spatula wherein the spatula includes a proximal end, a distal end, and a body wherein the distal end includes a planar wedge and the accessing includes sliding the substantially hollow spatula over the spinal pin while adjusting the rotation of the planar wedge until the planar wedge enters the facet joint; sliding a substantially hollow drill guide over the spatula wherein the drill guide includes a proximal end, a distal end, and a handle wherein the handle is nearer to the proximal end of the drill guide than to the distal end and wherein the distal end includes opposed teeth; removing the spinal pin and the spatula from within the drill guide; inserting a drill bit into the drill guide; drilling a hole into a bone of the facet joint; removing the drill bit; sliding an inserter instrument into the drill guide wherein the inserter instrument has a proximal end and a distal end, wherein a facet joint bone plug is associated with the distal end and wherein the proximal end includes a raised portion that prevents over-insertion of the facet joint bone plug; disengaging the facet joint bone plug from the distal end of the inserter instrument into the drilled hole; and removing the drill guide. In some embodiments, the method also includes confirming the location of the spinal pin at the facet joint, for example by taking at least one x-ray. In other embodiments, the method also includes tapping the spatula further into the facet joint following the initial entry of the planar wedge into the facet joint. In some embodiments, the method also includes tapping the drill guide so that the opposed teeth of the drill guide engage facet joint bone to secure the orientation of the drill guide until the removing of the drill guide. In some embodiments, the method also includes tapping the facet joint bone plug into the hole following the facet joint bone plug's disengagement from the inserter instrument. In some embodiments, the spatula and the drill guide each further includes a marking, wherein when the marking on the drill guide is matched or aligned with the marking on the spatula, the orientation of the opposed teeth is in approximately the same plane defined by the planar wedge. In some embodiments, the method also includes the step of matching or aligning the markings on the spatula and the drill guide. In some embodiments the distal end of the drill guide includes two opposed teeth. In some embodiments, the distal end of the drill guide includes a plurality of teeth, wherein the plurality of teeth includes two opposed teeth and one or more smaller teeth disposed between the two opposed teeth. In some embodiments, the drilling includes grinding the bone and compacting some of the drilled bone within the hole.

The present invention also includes surgical kits. In one embodiment according to the present invention the surgical kit includes a pin comprising a distal end and a proximal end and a substantially hollow drill guide wherein the drill guide includes a proximal end, a distal end, a handle and a marking wherein the handle is nearer to the proximal end of the drill guide than to the distal end and wherein the distal end includes opposed teeth and wherein the marking indicates the rotational orientation of the two opposed teeth. In some embodiments, there are two opposed teeth.

In another embodiment of a surgical kit according to the present invention the surgical kit further includes a bone plug.

An additional embodiment of a surgical kit according to the present invention includes a surgical kit comprising a substantially hollow spatula comprising a proximal end, a distal end, a body and a marking on the body wherein the distal end includes a planar wedge and the marking indicates the rotation of the planar wedge; and a drill guide comprising a proximal end, a distal end, a handle and a marking wherein the handle is nearer to the proximal end of the drill guide than to the distal end and wherein the distal end includes two opposed teeth and wherein when the marking on the drill guide is matched or aligned with the marking on the spatula when the drill guide is place over the spatula, the orientation of the opposed teeth is in approximately the same plane defined by the planar wedge.

Surgical kit embodiments according to the present invention can further comprise a tool selected from the group consisting of an inserter instrument, a spinal pin, a spinal needle, an impacter, a hammer, a drill bit, a drill, a reamer, a dilator, a bone plug holder, a bone plug, and an autoclavable surgical tool kit box.

One particular surgical kit according to the present invention includes a surgical kit comprising a substantially hollow spatula comprising a proximal end, a distal end, a body and wherein the distal end includes a planar wedge; and a drill guide comprising a proximal end, a distal end, and a handle wherein the handle is nearer to the proximal end of the drill guide than to the distal end and wherein the distal end includes opposed teeth. In some embodiments, the substantially hollow spatula includes a marking on the body. In some embodiments, the marking on the body of the spatula indicates the rotation of the planar wedge. In some embodiments, the distal end of the drill guide includes two opposed teeth. In some embodiments the drill guide includes a marking. In some such embodiments, the when the marking on the drill guide is matched or aligned with the marking on the spatula when the drill guide is place over the spatula, the orientation of the opposed teeth is in approximately the same plane defined by the planar wedge Additional embodiments of kits according to the present invention can also individually, collectively or in various combinations include one or more of a spinal pin, a spinal needle, an impacter, a hammer, a reamer, a drill bit, a reamer, a drill, a dilator, a dilator tube, a guide wire, a bone plug, and a bone plug holder wherein all components of the kit except for the reamer can be re-used, stored and sterilized in a single autoclavable surgical tool kit box.

In some embodiments the present invention includes a surgical kit including a substantially hollow spatula comprising a proximal end, a distal end, and a body wherein the distal end includes a planar wedge; and a drill guide comprising a proximal end, a distal end, and a handle wherein the handle is nearer to the proximal end of the drill guide than to the distal end and wherein the distal end includes opposed teeth; a spinal pin; a drill bit; a bone plug inserter comprising a proximal end and a distal end, wherein the distal end is configured to interact with a bone plug and wherein the proximal end includes a raised portion that prevents over-insertion of the bone plug; a bone plug holder; and wherein all components of the kit can be stored and sterilized in a single autoclavable tool box. In certain embodiments, the spatula and the drill guide each further includes a marking, wherein when the marking on the drill guide is matched or aligned with the marking on the spatula, the orientation of the opposed teeth is in approximately the same plane defined by the planar wedge. In particular embodiments, the marking on the spatula indicates the rotation of the planar wedge. In other embodiments, the surgical tool kit also includes a spinal needle, an impacter, a hammer, a drill, a reamer, a dilator or a bone plug. In some embodiments the drill bit is configured to grind the bone and compact some of the drilled bone within the hole.

The methods and surgical kits of the present invention described above can also be used or sold in conjunction with bone plugs according to the present invention. In one embodiment along the length of the bone plug there is at least one major diameter and at least one minor diameter. In another embodiment the bone plug includes a fin or a series of fins. In some embodiments, the fins in the series are spaced approximately 1 mm apart.

DETAILED DESCRIPTION OF THE INVENTION

Figure 1:
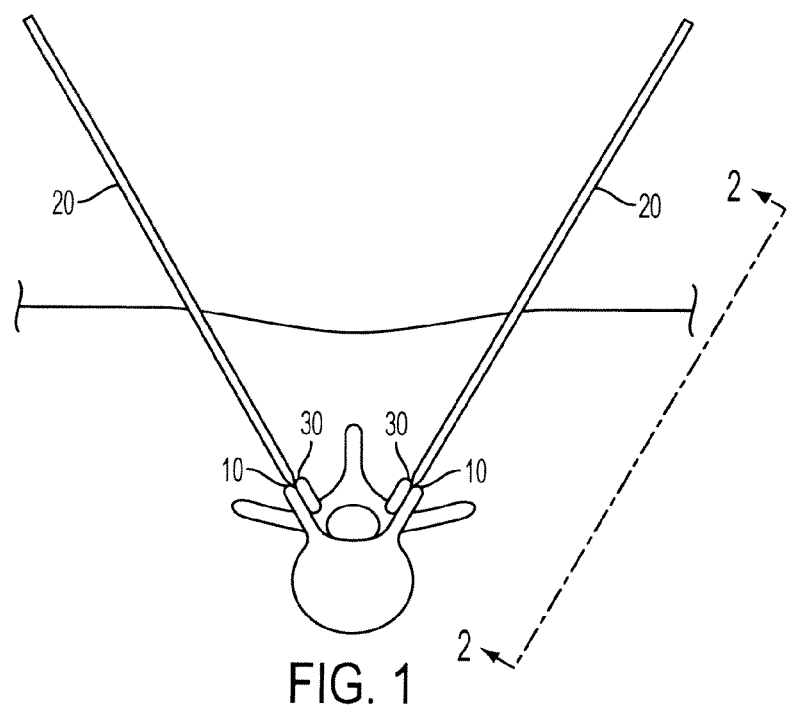
FIG. 1 shows facet joint location with surgical pins.

It is understood that the present invention is not limited to the particular methodologies, protocols, systems and methods, etc., described herein, as these may vary. It is also to be understood that the terminology used herein is used for describing particular embodiments only, and is not intended to limit the scope of the present invention. It must be noted that as used herein and in the appended claims, the singular forms "a," "an," and "the" include the plural reference unless the context clearly dictates otherwise. For instance, a reference to a surgical kit refers to one or more surgical kits and a reference to "a method" is a reference to one or more methods and includes equivalents thereof known to those of ordinary skill in the art and so forth.

Unless defined otherwise, all technical and scientific terms used herein have the same meanings as commonly understood by one of ordinary skill in the art to which this invention belongs. Specific methods, devices, systems and materials are described, although any methods and materials similar or equivalent to those described herein can be used in the practice or testing of the present invention.

Back pain is a prevalent problem in the United States. One root cause of back pain, particularly the persistent and disabling kind, is problems with facet joints. Each vertebra has two sets of facet joints. One pair faces upward and the other pair faces downward. Within each set there is a facet joint on the left side of each vertebra and a facet joint on the right side of each vertebra.

Facet joints, also called zygapophyseal or apophyseal joints are the system of joints that allow movement (forward bending, backward bending and twisting) of the spine. While these joints allow movement of the spine, their interlocking nature also helps to stabilize the spine.

Similar to other joints in the body, each facet joint is surrounded by a capsule of connective tissue and produces synovial fluid to nourish and lubricate the joint. The joint surfaces themselves are coated with a thick spongy material called articular cartilage that enables the bones of each joint to smoothly move against the other.

Osteoarthritis is one cause of facet joint pain. This degenerative disease causes progressive cartilage deterioration. Without the spongy cartilaginous cushion, joint bones rub against each other when at rest and during movement causing a substantial amount of pain. Therefore, one option to treat this type of pain is to join rubbing portions of bone together so that this painful friction does not occur.

The present invention provides a minimally-invasive surgical option and associated tools to fuse facet joints for the treatment of back pain. The methods and tools can be used to perform the joint fusion in a minimally invasive procedure, for example arthroscopically or percutaneously, in some instances, leading to an out-patient procedure. In one embodiment, the methods and tools can be used to fuse the forty-eight spinal facet joints on the spine from C1-C2 through L5-S1.

Figure 2:
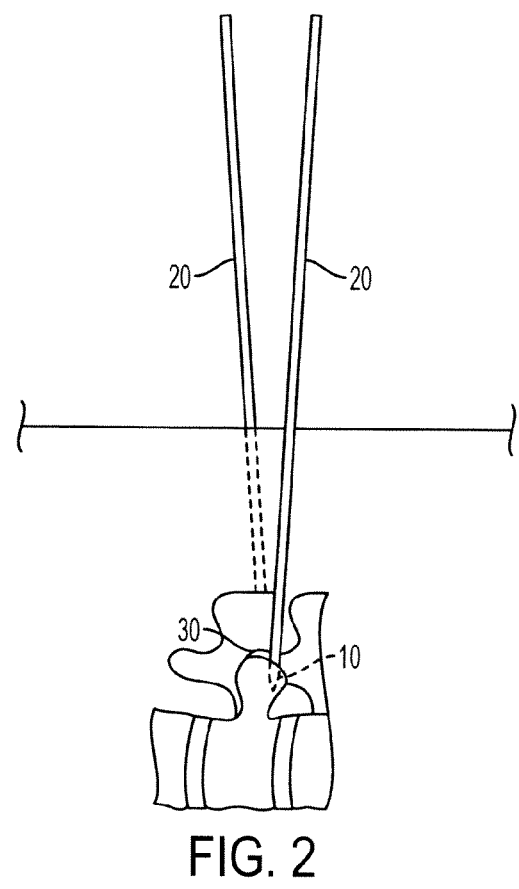
FIG. 2 shows an alternative view of facet joint location with surgical pins.

Turning to the Figures, FIG. 1 represents a first step in the presently-described procedure. In this step, following the creation of a small incision, the distal tips 10 of surgical pins 20 are used to locate facet joints 30. FIG. 2 depicts an alternative view of FIG. 1 showing the location of facet joints 30 with distal ends 10 of pins 20.

Figure 3:
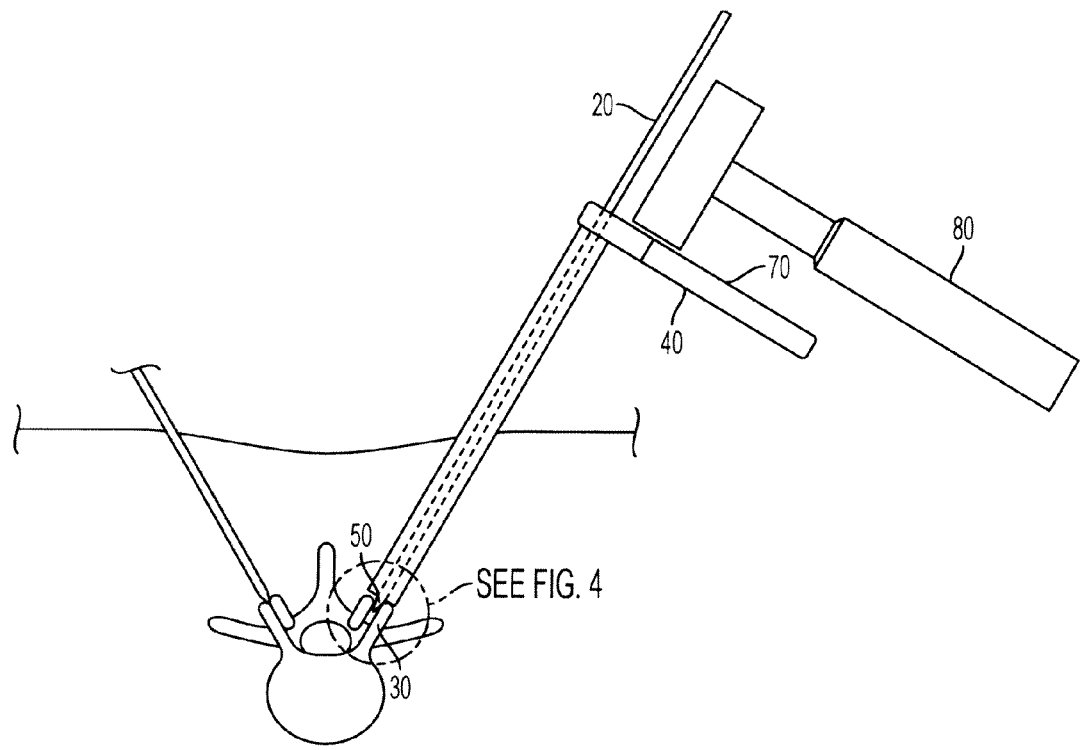
FIGS. 3-5 depict insertion of a drill guide directly over a surgical pin without the use of a spatula.

Once the facet joint 30 has been located with the distal end of a pin 20, as seen in FIG. 3, a substantially hollow drill guide 40 can be slid over the pin 20. The drill guide 40 can reach the facet joint 30 through progressive dilation of the intervening soft tissue (note, however, that the instrument design does not preclude its use in a classic open surgery or by access to the facet joint through an otherwise limited incision).

Figure 4:
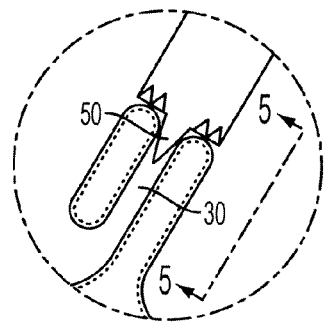
Figure 5:
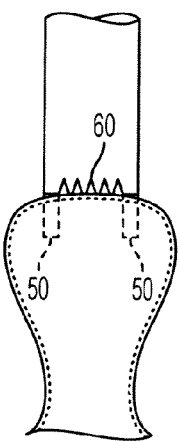

FIG. 4 depicts an enlarged view of the distal end of the drill guide within a facet joint 30. The distal end of the drill guide 40 can have one of more teeth 50. In certain embodiments, the distal end of the drill guide 40 has two larger teeth 50 (FIG. 5) that are separated by about 180° around the circumference of the distal end of the drill guide 40. In certain embodiments, the drill guide 40 can have a marking that indicates the rotational orientation of these two teeth 50. One or more smaller teeth 60 may also be found between or surrounding the larger teeth 50. In general, the two larger teeth 50 may be inserted into the facet joint 30 as shown in FIGS. 3, 4 and 5. To achieve this insertion, the distal end of the drill guide 40 may simply be inserted into the facet joint 30. Alternatively or in combination, the handle 70 of the drill guide 40 may be tapped or hammered with a surgical hammer 80 to achieve insertion of the distal end of the drill guide into the facet joint 30.

Figures 6, 7, 8:
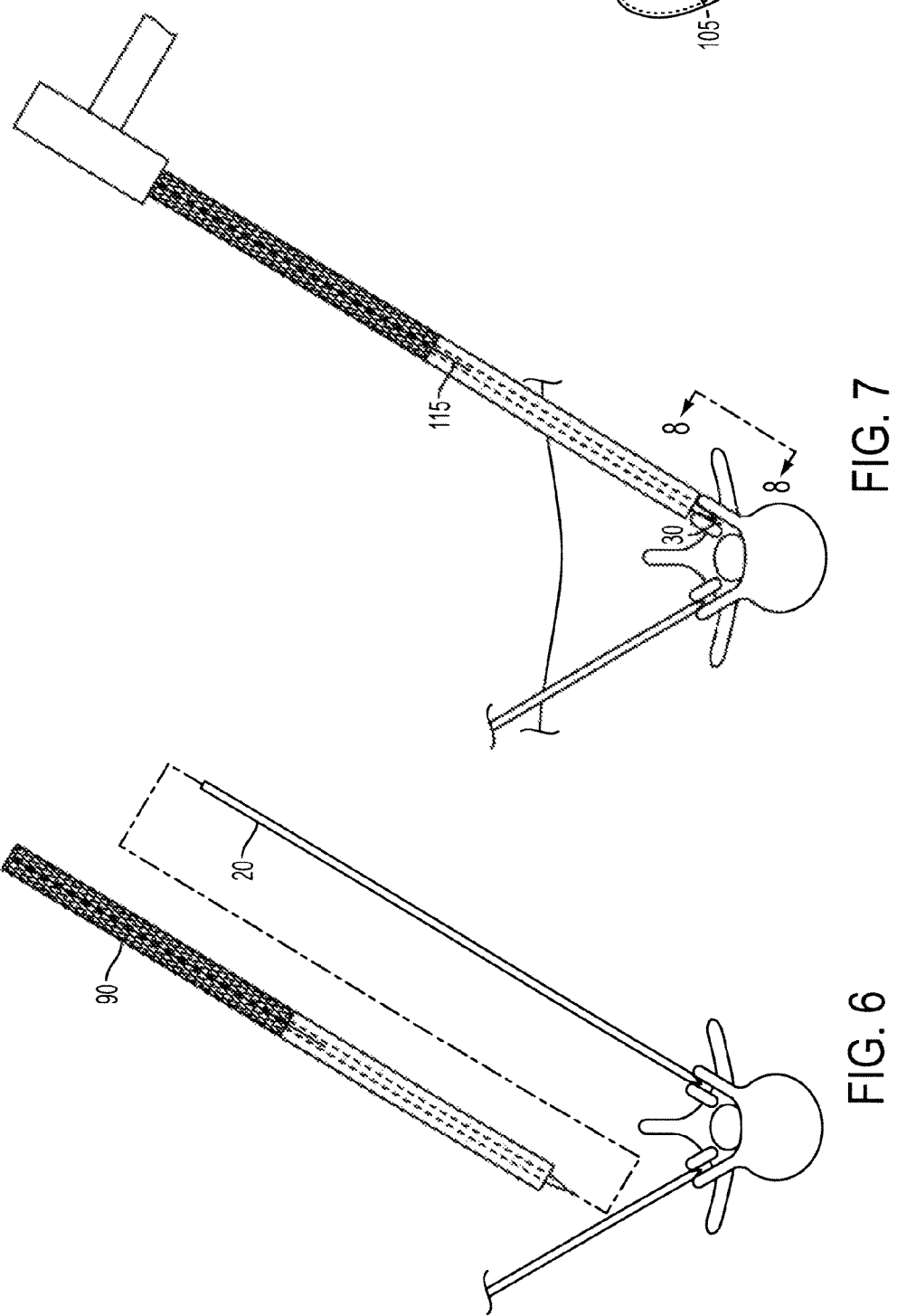
FIGS. 6-8 show the insertion of a spatula with a planar distal tip into the facet joint.
Figure 10:
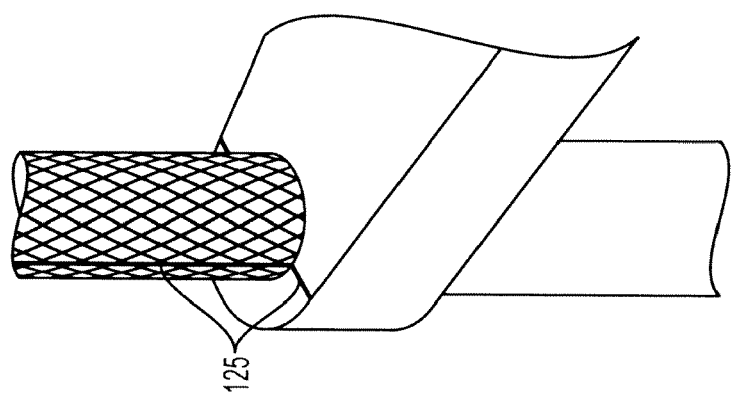
FIG. 10 depicts the alignment of markings on a spatula and drill guide to match the orientation of the distal ends of these tools.
Figure 9:
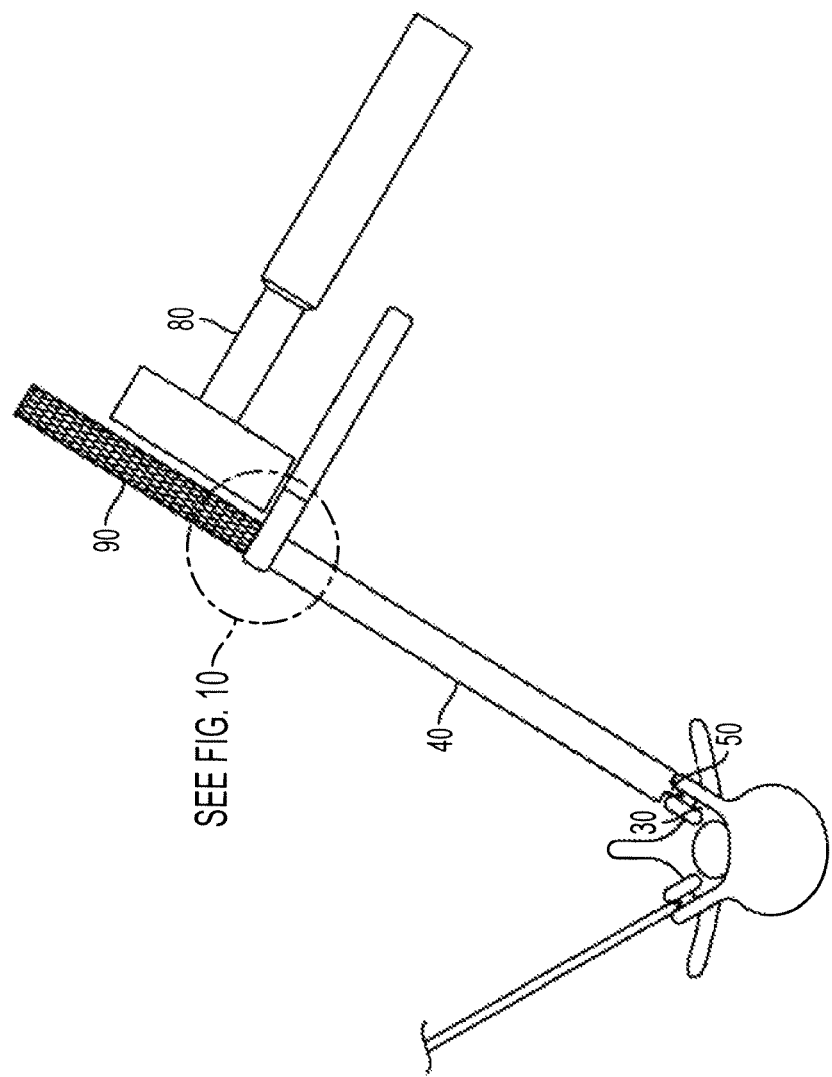
FIG. 9 depicts insertion of the drill guide over the spatula.

In a particular embodiment of the present invention, there can be an intermediate step between locating the facet joint 30 with the distal end 10 of a pin 20 and inserting the drill guide 40 over the pin 20. In this alternative embodiment, depicted in FIGS. 6-8, a substantially hollow spatula 90 is inserted over the pin 20. The distal end of the spatula 90 can have a planar wedge 105 that can be inserted into the facet joint 30. The spatula 90 may also have a marking 115 that can indicate the orientation of the planar wedge once inserted into the body. In this embodiment, and as shown in FIG. 9, after the planar wedge of the spatula 90 is inserted into the facet joint 30, the drill guide 40 can be inserted over the spatula 90. When both the spatula 90 and the drill guide 40 are inserted, the markings on each 125 can be aligned so that the rotational orientation of the drill guide's two larger teeth 50 is in approximately the same plane defined by the spatula's planar wedge (FIGS. 9 and 10). If the planar wedge of the spatula 90 is inserted into the facet joint 30, then lining up the markings 125 on the spatula 90 and drill guide 40 will place the drill guide's two larger teeth 50 in the proper orientation to also enter the facet joint 30. Once aligned in this manner, the two larger teeth 50 can simply be inserted into the facet joint 30. Alternatively, or in combination, and as shown in FIG. 9, a surgical hammer 80 or other appropriate tool may be used to tap or hammer the drill guide 40 into place within the facet joint 30.

Figure 11:
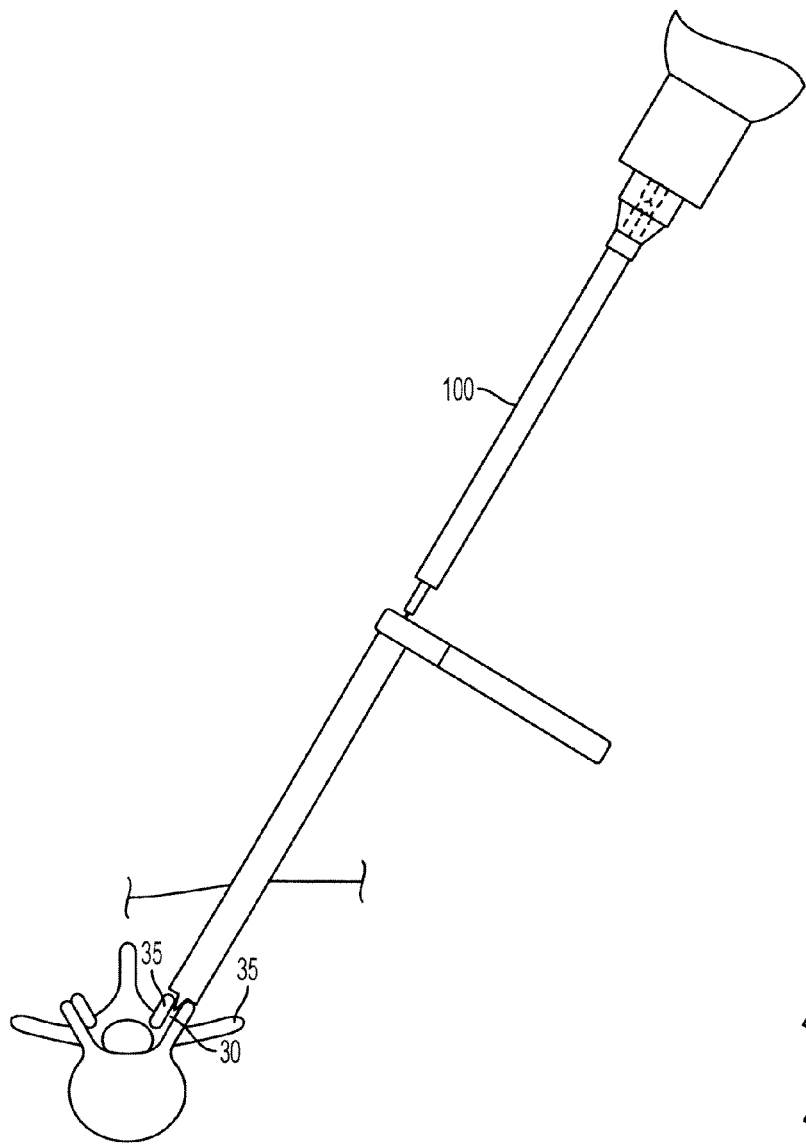
FIG. 11 shows the drill guide in position following removal of the surgical pin and/or spatula with a drill bit ready for insertion into the drill guide.
Figure 12:
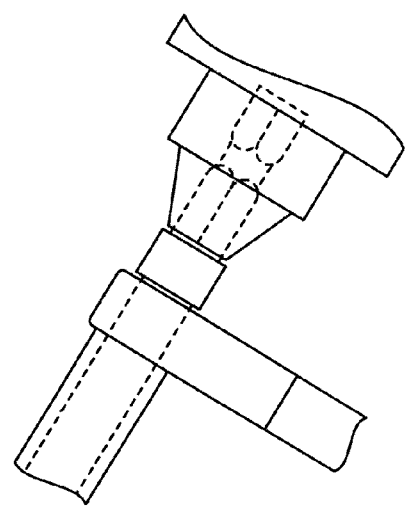
FIG. 12 shows an enlarged view of insertion of a drill bit into the drill guide.

Regardless of whether spatula 90 is used, following insertion of the distal end of the drill guide 40 into the facet joint 30, the pin 20 and/or spatula 90 can be removed from the substantially hollow inner portion of the drill guide 40. Following this removal, an appropriately-sized drill bit 100 is inserted through the substantially hollow portion of the drill guide 40. The drill bit 100 is used to create a hole between the bones 35 of facet joint 30 (see FIGS. 11 and 12). In some embodiments, the drill bit drills the hole in a manner that permits at least some of the drilled bone to remain in the hole. In some such embodiments, the drill grinds the drilled bone into a powder as it creates the hole. In some such embodiments, the drill bit compacts the drilled bone into the bone forming the hole. This compacted bone that remains in the drilled hole may help fusion of the facet joint by facilitating bone growth within the hole. The described drill bit (a punch could also be used) includes any number of components capable of performing the creation of a hole through both sides of the spinal facet joint.

Figure 13:
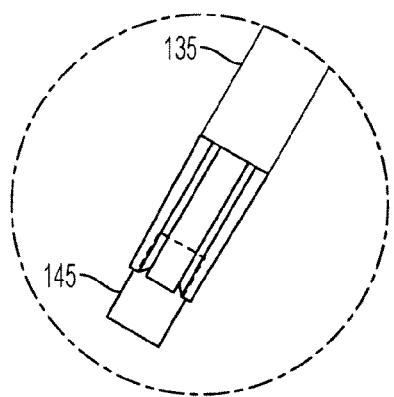
FIG. 13 shows an enlarged view the distal tip of a bone plug inserter with a bone plug ready for deployment.
Figure 14:
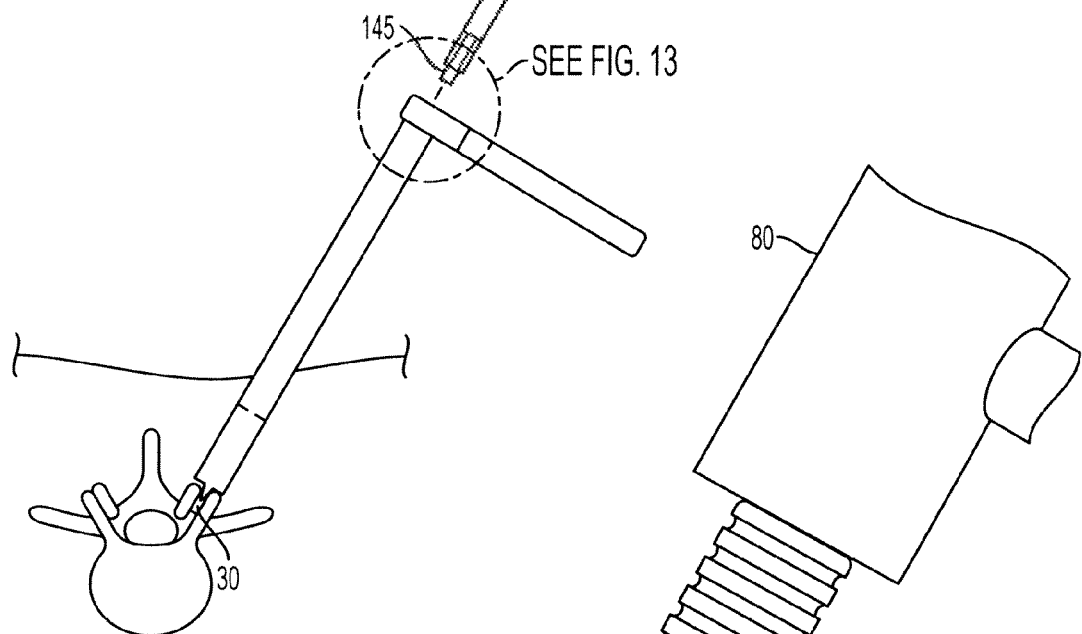
FIG. 14 shows the bone plug inserter of FIG. 13 ready for insertion through the drill guide.
Figure 15:
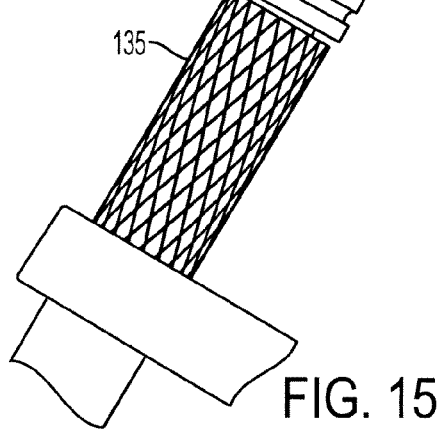
FIG. 15 represents the tamping or hammering of the proximal end of the inserter once inserted through the drill guide.

As shown in FIG. 14, following the creation of a hole in the facet joint 30 a bone plug inserter 135 can be used to place a bone plug 145 into the hole. FIG. 13 shows an enlarged view of the distal end of a bone plug inserter 135 and its associated bone plug 145. As shown in FIG. 15, the bone plug 145 can simply be inserted into the facet joint 30, or, alternatively, or in combination, a surgical hammer 80 or other appropriate tool may be used to tap or hammer the bone plug inserter 135 to fix the bone plug 145 within the facet joint 30. Furthermore, any number of additional components capable of pushing and/or compressing a bone plug 145 into the hole can additionally be used. In certain particular embodiments, a suture or metallic overlay can also be applied to provide additional structural stability to the joint during bone plug 145 incorporation.

Figure 16:
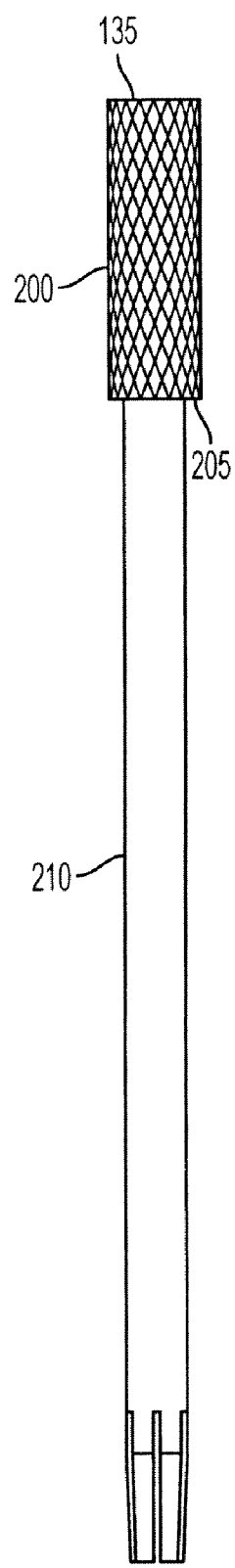
FIG. 16 shows a alternative design of a bone plug inserter that can be used in accordance with the present invention.

A specific embodiment of a bone plug inserter 135 is depicted in FIG. 16. In this embodiment, bone plug inserter 135 comprises a raised portion 200 at or near its proximal end. Raised portion 200 has dimensions that are greater than those of elongate portion 210. For example, in an embodiment where bone plug inserter 135 is substantially cylindrical, raised portion 200 may have a diameter greater than that of elongate portion 210. Raised portion 200 is configured to interact with the proximal portion of drill guide 40 in a manner that prevents passage of raised portion 200 into the substantially hollow portion of the drill guide 40. In a specific embodiment, the distal edge or surface of raised portion 200 at lip or ridge 205 contacts the proximal end of the drill guide 40. This configuration minimizes the chances of over-insertion of bone plug 110 into hole 28 and related damage. Over insertion in this context includes insertion of the bone plug 110 into hole to an extent that may cause damage to the bone plug 110, hole 28, or any portion of the facet joint. In some embodiments, over insertion occurs where the bone plug 110 is inserted to an extent that causes the distal end of the bone plug 110 to extend beyond the facet joint or proximal end of the bone plug 110 to be below the surface of the facet joint. Raised portion 200 may be any suitable size and configuration. For example, raised portion 200 may simply be a post or other structure that is configured to interact with the distal portion of drill guide 40.

Figure 17:
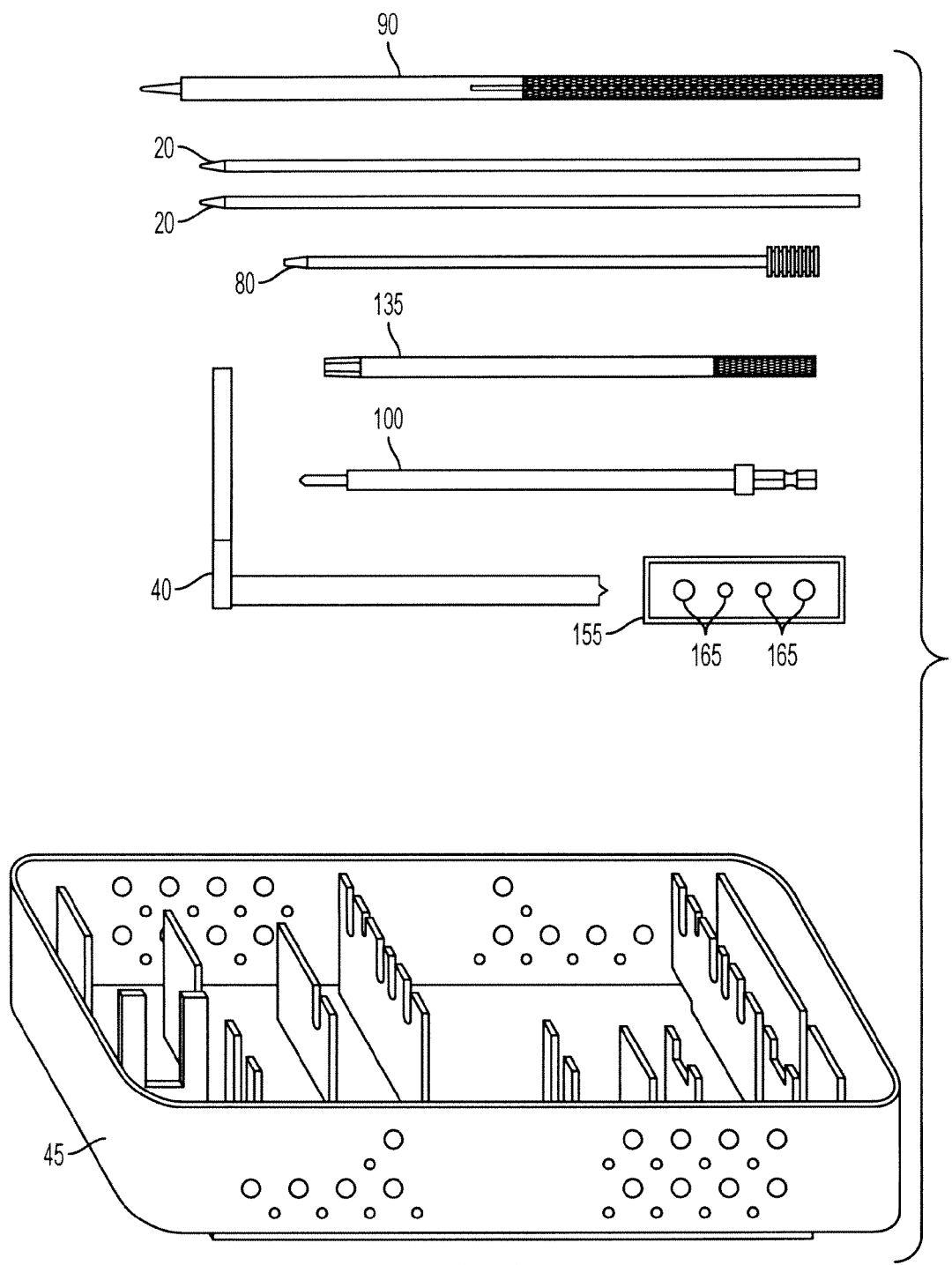
FIG. 17 shows surgical tools that can be used in accordance with the present invention in a combination that may be provided in a surgical kit.

FIG. 17 depicts tools that can be assembled into a surgical kit of the present invention. The depicted surgical kit includes pins 20, a spatula 90, a drill guide 40, a surgical hammer 80, a bone plug inserter 135, an appropriately-sized drill bit 100 and a bone plug holder 155. The depicted bone plug holder 155 has openings 165 shaped to hold variously sized or shaped bone plugs. Other surgical kits according to the present invention can include different combinations or subsets of these tools in varying numbers as deemed appropriate for particular needs and uses. Whatever combination of tools is chosen for a particular surgical kit according to the present invention, the tools are generally provided in an autoclavable container such as or similar to that depicted in FIG. 17. The tools may be configured such that they may be used in minimally invasive procedures (e.g., arthroscopic or percutaneous procedures).

Figure 18:
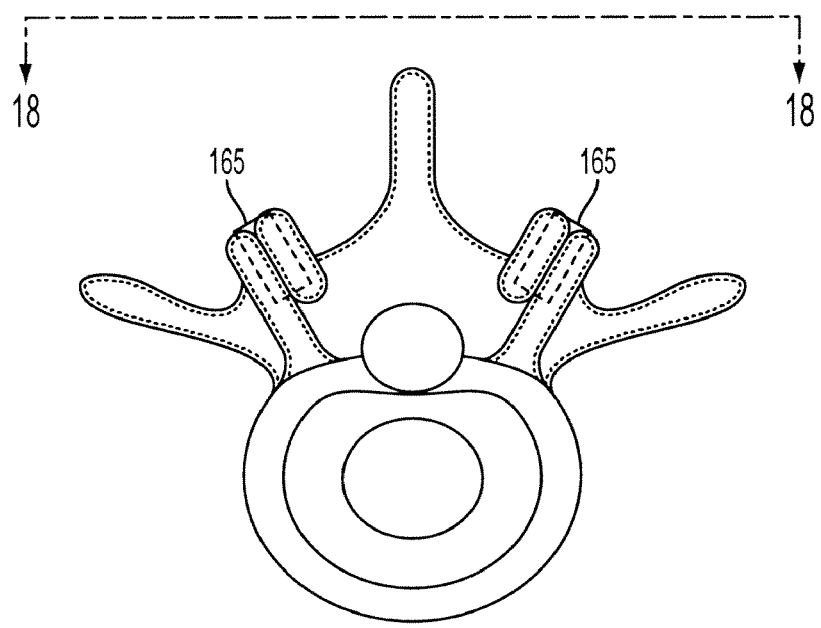
FIGS. 18 and 19 represent alternate views of holes created by drilling in the facet joints where bone plugs of the present invention can be inserted.
Figure 19:
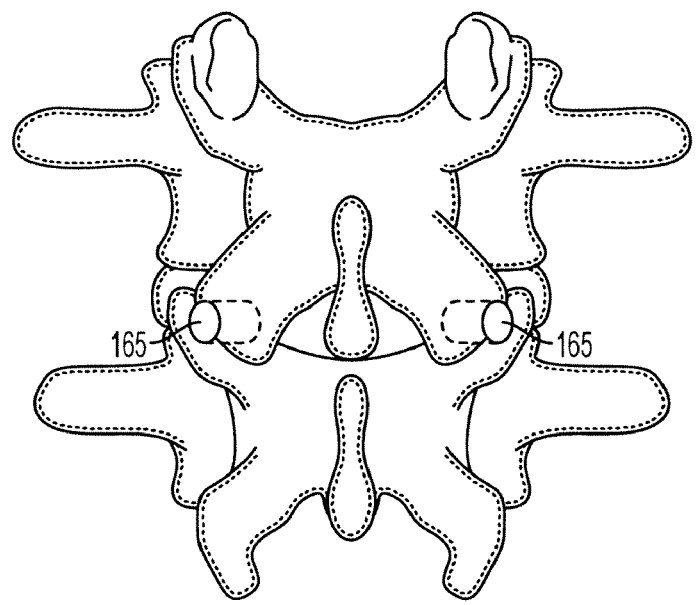

Holes 165 in facet joints created by the previously described drill bit are depicted in FIGS. 18 and 19. An alternative depiction of a hole 28 created by a drill bit in a facet joint between two facet joint bones 130 and 32 is provided in FIG. 20.

Figure 20:
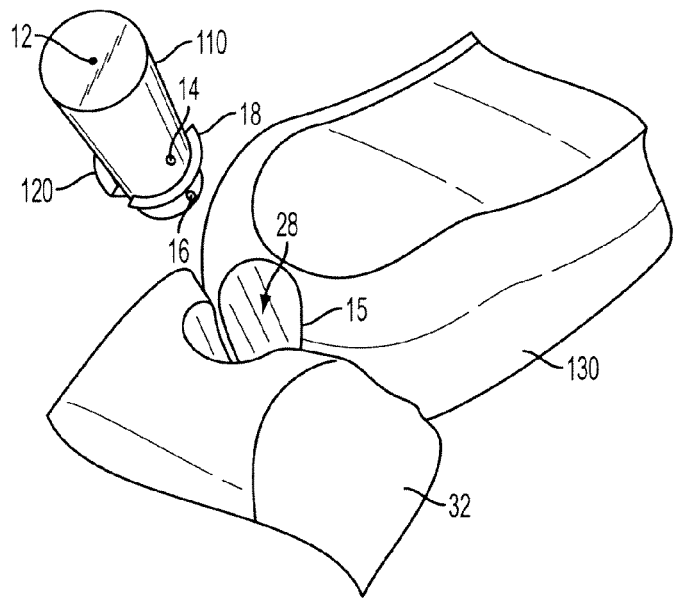
FIG. 20 shows an alternative representation of a hole prepared for insertion with a bone plug oriented for insertion into the hole.

This FIG. 20 also shows one embodiment of a bone plug 110 according to the present invention. This bone plug 110 according to the present invention has fins or flanges 18 and 120 that can assist in holding the bone plug 110 within the created hole 28. Moreover, the depicted bone plug 110 has holes 12, 14 and 16 which connect channels within the bone plug 110. These holes 12, 14 and 16 and associated channels permit the insertion of synthetic or biologic materials into and around bone plug 110 following its placement within the facet joint.

Figure 21:
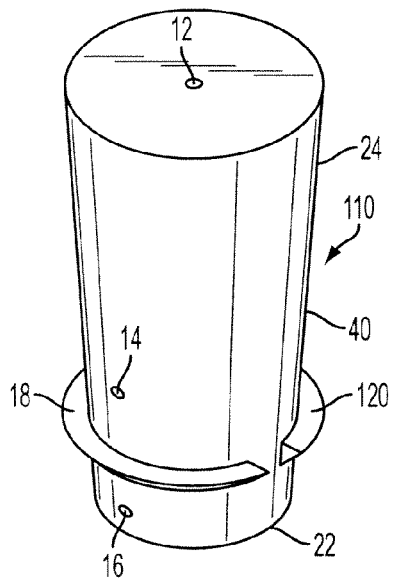
FIG. 21 shows a frustum shaped bone plug of the present invention that can be used in facet joint fusion.

The bone plug 110 depicted in FIG. 20 is also shown in an enlarged alternative perspective in FIG. 21. This depicted bone plug 110 includes an inverted frustum shape with a pair of opposed fins or flanges 18 and 120 on the same plane that can partially circumvent the bone plug 110 near bottom end 22 which has a smaller diameter than the top end 24. In certain embodiments according to the present invention, the distal end 22 of the bone plug 110 can be about 3 mm to about 8 mm in diameter and the proximal end 24 of the bone plug can be about 4 mm to about 12 mm in diameter. This general shape can be adopted to facilitate fixation during bone plug incorporation into the facet joint. The procedure is envisioned to require only one bone plug per facet joint and, if required, two bone plugs per facet joint level. Permanent fixation of the bone plugs should occur when bone in-growth occurs into the joint itself and into the plug over time.

Still referring to FIG. 21, bone plug 110 has a vertical central channel extending generally downwardly from opening 12 that can be used, when desired, for insertion of synthetic and/or biologic materials. These synthetic and/or biologic materials can be used for a variety of purposes including, without limitation, to resist infection, reduce inflammation and/or to assist in fusing the bone plug 110 in place within the facet joint. As shown, the bone plug 110 can have multiple channel openings 12, 14 and 16 on its surface that can be used to deliver the synthetic and/or biologic materials to various locations of the facet joint. The depicted bone plug 110 also includes a fin or flange 18 as an optional anti-migration feature. The depicted bone plug 110 also includes fins or flanges 18, 120 as optional anti-migration features.

Figure 22:
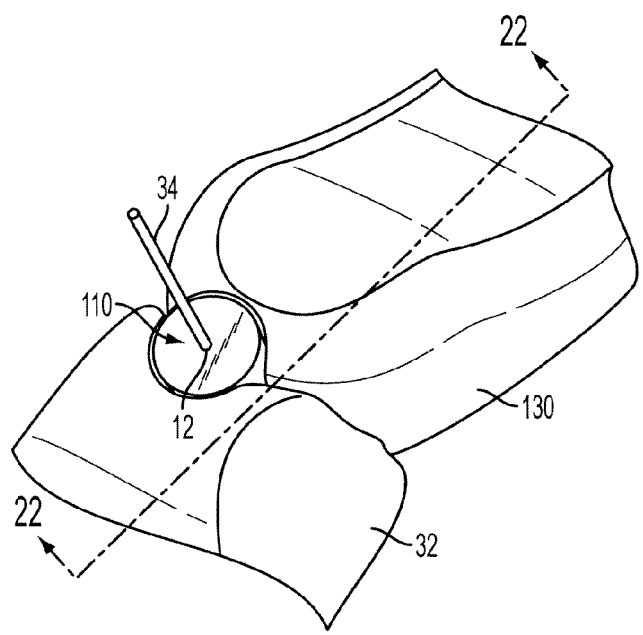
FIG. 22 shows a bone plug inserted in the hole of FIG. 20 with an application tube for inserting synthetic or biologic material into the facet joint.
Figure 23:
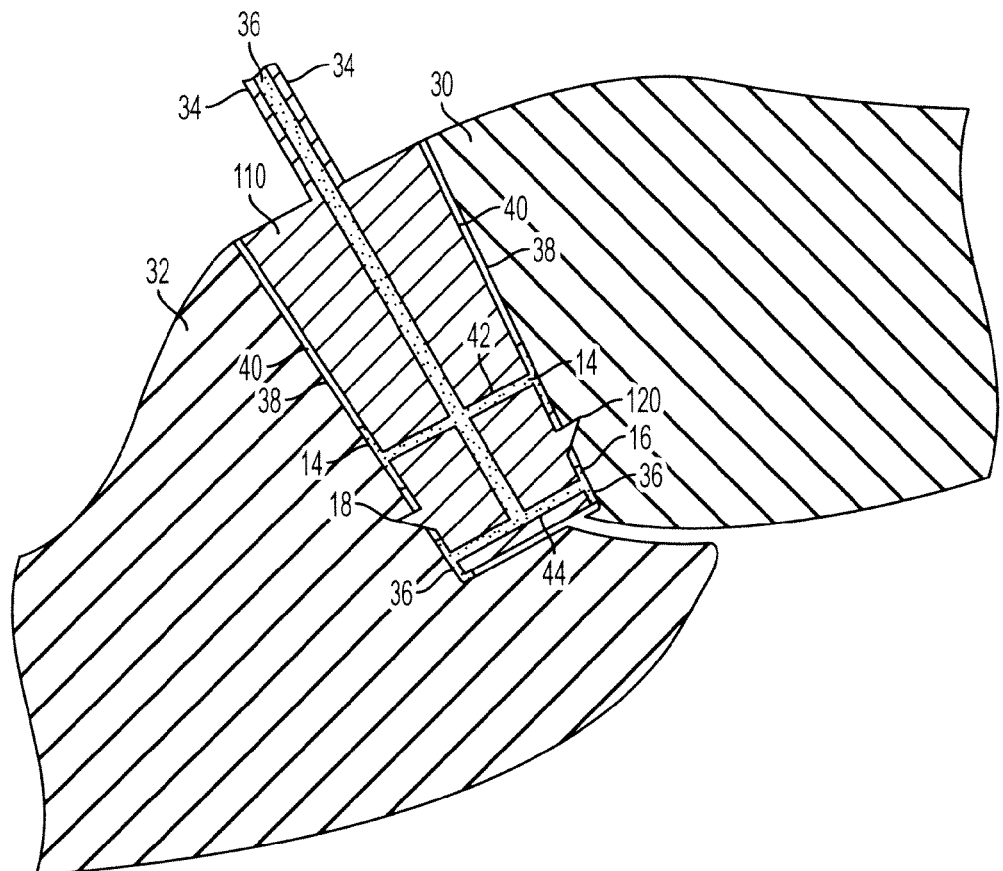
FIG. 23 is a cross-section depiction of FIG. 22.

FIG. 22 shows a bone plug 110 inserted into a facet joint between facet joint bones 130, 32. A synthetic and/or biologic material delivery device 34 that can be used to administer the chosen synthetic and/or biologic materials is also shown. FIG. 22 depicts a cross section of this bone plug within the facet joint. As shown, an application tube 34 can be placed over the top of and/or inserted into a channel that extends generally downwardly from opening 12 to permit insertion of synthetic and/or biologic materials 36 into bone plug 110. When administered, the synthetic and/or biologic materials 36 can flow down the channel associated with opening 12 and into channels 42 and 44 and excess synthetic and/or biologic material will flow out of openings 14 and 16 respectively, into a space 38 between the bones 130 and 32, and an exterior side wall 40 of the bone plug 110. Again, and in this particular embodiment, flanges 18 and 120 can act as fins or flanges to hold the bone plug 110 in place within the facet joint hole.

Figure 24:
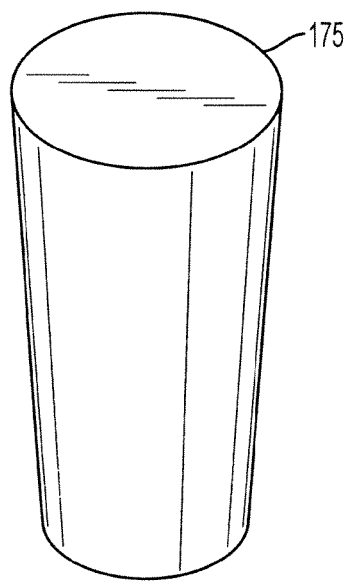
FIG. 24 shows a second alternative frustum shaped bone plug.
Figure 25:
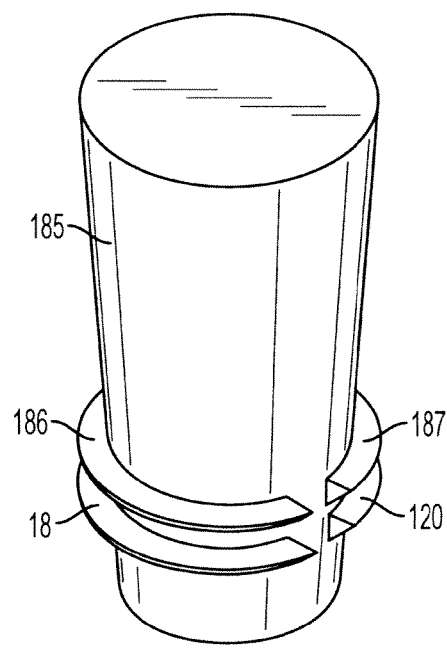
FIGS. 25-29 show a variety of bone plugs in with different configurations of fins, flanges and/or ridges.
Figure 26:
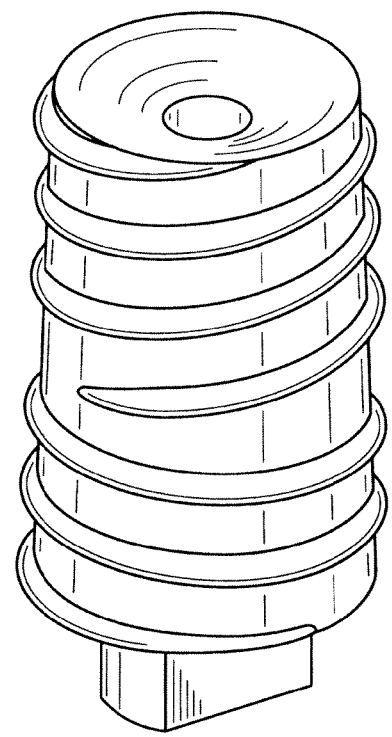
Figure 27:
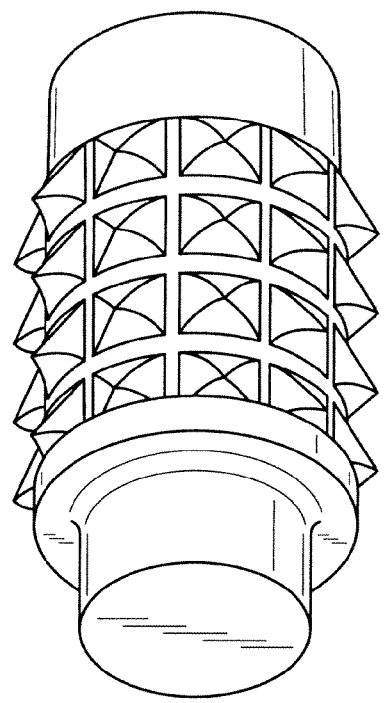
Figure 28:
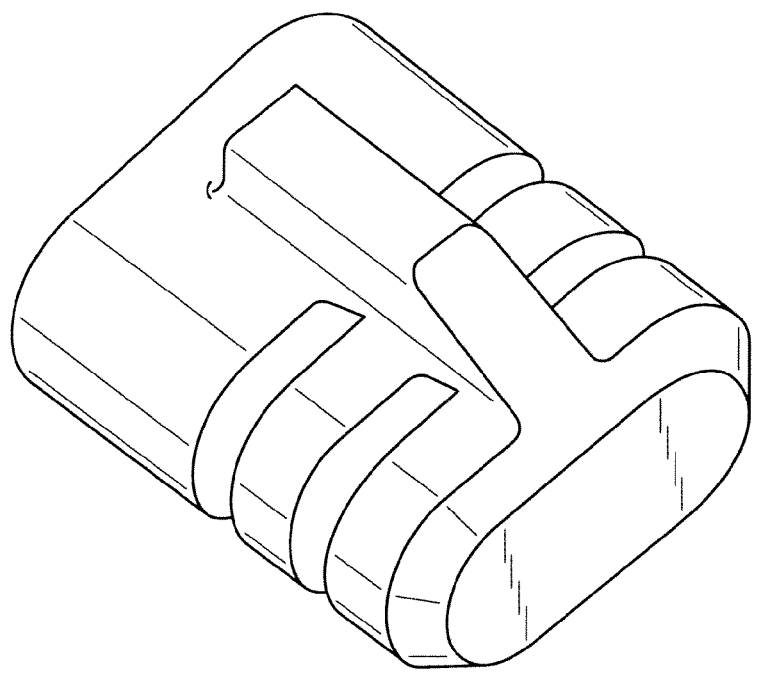
Figure 29:
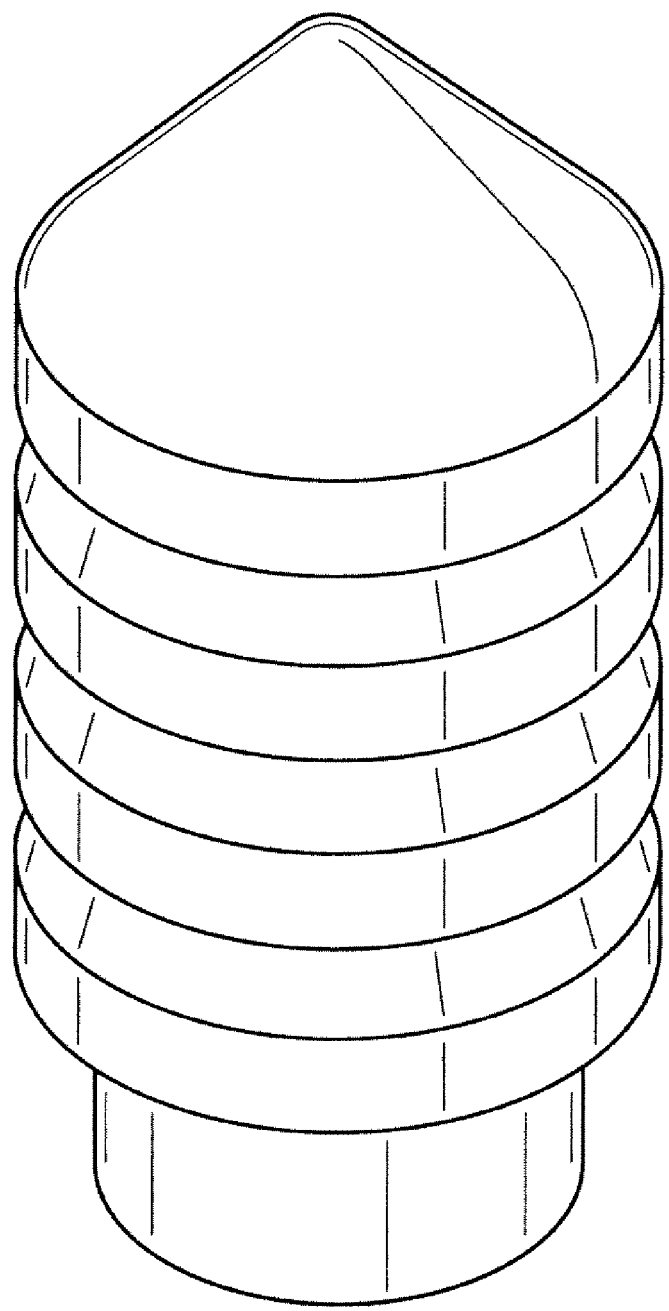

FIG. 24 shows an alternative bone plug 175 of the present invention. This bone plug 175 is similar to that previously described except that the bone plug 175 does not include channels for the delivery of synthetic and/or biologic materials or flanges. As should be understood by reference to FIG. 24, bone plugs according to the present invention are not required to adopt these features as they are not required to successfully practice the methods of the present invention. FIG. 24 shows another alternative bone plug 185 according to the present invention. This embodiment includes four fins or flanges 18, 120, 186, 187. FIGS. 26-29 show a variety of other bone plug designs for use in accordance with the present invention. Each design includes a different non-limiting example of a configuration of shapes, fins, flanges and/or ridges as features that can be used and incorporated into the bone plugs used with the present invention.

As should be understood by one of ordinary skill in the art, a bone plug of any appropriate shape, size or number of fins or flanges can be used in accordance with the present invention, including a bone plug without fins, ridges, flanges or other such structures.

Bone plugs according to the present invention can be formed of any suitable material. It should be understood that while the plugs according to the present invention are consistently referred to as "bone" plugs, they need not be formed out of bone in all circumstances. The key feature of these bone plugs is that they are formed of a material allowing bone in-growth and fixation over time. In some embodiments, the bone plugs of the present invention can be formed at least in part of any of the following: synthetic cortical bone, a harvested compacted synthetic iliac crest graft, an autologous allograft, a cadaveric allograft, autografts, bone substitutes such as coral granules or hydroxyapatite crystals, a trabecular or porous metal, a metal graft, synthetic iliac crest graft, a xenograft, synthetic graft, cortico-cancellous graft, and bone morphogenic proteins. In some embodiments, the bone plugs may also include or comprise proteins that enhance or promote bone growth. In one embodiment, the hole created in a facet joint can be filled with the patient's own harvested and compacted bone plug using iliac crest autograft. In other embodiments, the hole created in a facet joint can be filled with a pre-made, pre-shaped cortical cadaveric allograft (the autograft or allograft formed by bone plug press or machining). In further embodiments, the hole created in a facet joint can be filled with a FDA approved pre-made, pre-shaped synthetic graft.

In some embodiments, the bone plugs may include biocompatible granules, which are a hard substance that provides structural support or physiological advantages to the implant mass. The biocompatible granules can be made of synthetic, naturally occurring, polymeric, or non-polymeric materials. In one embodiment, the granules are also biodegradable such that the implant degrades over time and may be replaced with native bone tissue. The biocompatible granules of the present invention can be made of a synthetic, biocompatible material, such as biopolymers, bioglasses, bioceramics, calcium sulfate, silicon oxide, calcium phosphate such as, for example, monocalcium phosphate monohydrate, monocalcium phosphate anhydrous, dicalcium phosphate dihydrate, dicalcium phosphate anhydrous, tetracalcium phosphate, calcium orthophosphate phosphate, calcium pyrophosphate, α-tricalcium phosphate, β-tricalcium phosphate (β-TCP), apatite such as hydroxyapatite (HA), or polymers such as, for example, poly(α-hydroxyesters), poly(ortho esters), poly (ether esters), polyanhydrides, poly(phosphazenes), poly (propylene fumarates), poly(ester amides), poly(ethylene fumates), poly(amino acids), polysaccharides, polypeptides, poly(hydroxy butyrates), poly(hydroxy valerates), polyurethanes, poly(malic acid), polylactides, polyglycolides, polycaprolactones, poly(glycolide-co-trimethylene carbonates), polydioxanones, or copolymers, terpolymers thereof or blends of those polymers, or a combination of biocompatible and biodegradable materials.

The following materials can also be used as a structural component in the bone plugs of the present invention and are considered to be synthetic materials: Chitin and chitosan, which may be derived form tissues of marine non-vertebrate animals; hyaluronic acid, a polysaccharide, which can be obtained from rooster comb or by microorganism fermentation; poly(amino acids) and polypeptides, which may be produced by biotechnological processes; any polysaccharide, which is obtained from plants, from non-vertebrate animals or by biotechnological processes (e.g. alginate).

Calcium phosphate ceramics are biocompatible and can be used in various biomedical applications. HA and β-TCP bioceramics are particularly useful materials because they have similar ionic properties as the mineral components of bone. In addition, their resorption kinetics can be controlled to meet the needs of a specific therapy. Furthermore, because β-TCP is biodegradable, it is absorbed in vivo and can be replaced with new bone growth.

Other equivalent elements can be substituted for the elements disclosed herein to produce substantially the same results in substantially the same way.

It is anticipated that the availability of the methods and surgical kits described herein will dramatically increase the number of surgeries performed because they can offer the first safe outpatient surgical solution to the predominant cause of spinal joint pain. It is expected that many patients receiving this procedure will be able to walk out the same day and be fully functional within a few weeks. Present surgical solutions require hospitalization of about three days and six to twenty-four months recovery.

Aside from the obvious positive clinical outcome, the significant favorable financial impact on disability, worker's compensation and health care insurers is considerable. First, the present invention provides a minimally invasive surgery that often can be performed in an outpatient setting as opposed to major surgery performed in a hospital. This procedure can also be performed during open surgery if the facet joints need to be fused as determined by a physician particularly in conjunction with instrumented vertebral fusion. Second, recovery times are estimated to be a few weeks as opposed to 6 to 12 months, and finally, the present invention is directed at overcoming, or at least improving upon, the disadvantages of the prior art by achieving the following: reduced morbidity; reduced blood loss; reduced time under anesthesia; reduced risk; reduced recovery time; reduced risk of post-operative infection; and minimal scarring that decreases the risk of failed back syndrome and improves revision surgery outcome. Furthermore, the present invention does not preclude other surgical or non-invasive treatment options.

While specific embodiments of the present invention have been described, other and further modifications and changes may be made without departing from the spirit of the invention. All further and other modifications and changes are included that come within the scope of the invention as set forth in the claims. The disclosures of all publications cited above are expressly incorporated by reference in their entireties to the same extent as if each were incorporated by reference individually.

What is claimed is:

1. A method comprising: creating an incision; locating a facet joint with a distal end of a pin by inserting said pin into said facet joint wherein said facet joint is formed between two opposing bones and said pin comprises said distal end and a proximal end;
   sliding a substantially hollow spatula over said pin wherein said spatula comprises a proximal end, a distal end, a channel and a body wherein said distal end comprises a planar wedge; the planar wedge adapted to enter and distract a patient's joint; wherein the channel extends along the length of the substantially hollow spatula from the proximal end of the substantially hollow spatula to the distal end of the substantially hollow spatula, the channel is parallel to the longitudinal axis of the substantially hollow spatula;
   adjusting the rotation of said planar wedge until said planar wedge enters said facet joint; sliding a substantially hollow drill guide over said spatula wherein said drill guide comprises a proximal end, a distal end, and a handle wherein said handle is nearer to the proximal end of the drill guide than to the distal end, said distal end comprises opposed teeth that can be inserted into said facet joint; removing said spatula from within said drill guide; inserting a drill bit into said drill guide; drilling a hole into a bone of said facet joint; removing said drill bit; inserting a facet joint bone plug into said hole using a bone plug inserter having a raised portion at or near its proximal end, wherein said raised portion prevents over-insertion of said bone plug; and; removing said drill guide; and closing said incision wherein said pin has also been removed prior to said closing of said incision.

2. A method according to claim 1 wherein the distal end of the drill guide comprises two opposed teeth.

3. A method according to claim 1 wherein said distal end of said drill guide comprises a plurality of teeth, wherein the plurality of teeth comprises two opposed teeth and one or more smaller teeth disposed between said two opposed teeth.

4. A method according to claim 1 further comprising confirming the location of said pin at said facet joint.

5. A method according to claim 4 wherein said confirming is accomplished with at least one x-ray.

6. A method according to claim 1 wherein said body of said spatula comprises a marking that can indicate the orientation of said planar wedge.

7. A method according to claim 6 wherein when said spatula further comprises a marking and wherein when said marking on said drill guide is matched or aligned with said marking on said spatula, the orientation of said opposed teeth is in approximately the same plane defined by said planar wedge.

8. A method according to claim 7 further comprising the step of aligning said markings on said spatula and said drill guide.

9. A method according to claim 1 wherein said inserting of said facet joint bone plug into said hole comprises sliding an inserter instrument into said drill guide wherein said inserter instrument has a proximal end and a distal end and a facet joint bone plug associated with said distal end; and disengaging the facet joint bone plug from said distal end of said inserter instrument into said drilled hole.

10. A method according to claim 1 further comprising tapping said spatula further into said facet joint following the initial inserting of said planar wedge into said facet joint.

11. A method according to claim 1 further comprising tapping said drill guide following said aligning of said markings so that said opposed teeth of said drill guide engage facet joint bone to secure the orientation of said drill guide until said removing of said drill guide.

12. A method according to claim 1 further comprising tapping said facet joint bone plug into said facet joint following said inserting.

13. A method according to claim 1 wherein said drilling comprises grinding the bone and compacting some of the drilled bone within said hole.

14. A method comprising: creating an incision; locating a facet joint with a spinal pin by inserting said spinal pin into said facet joint; accessing said facet joint with a substantially hollow spatula wherein said spatula comprises a proximal end, a distal end, a channel and a body wherein said distal end comprises a planar wedge; the planar wedge adapted to enter and distract a patient's joint; wherein the channel extends along the length of the substantially hollow spatula from the proximal end of the substantially hollow spatula to the distal end of the substantially hollow spatula, the channel is parallel to the longitudinal axis of the substantially hollow spatula, and
   said accessing comprises sliding said substantially hollow spatula over said spinal pin while adjusting the rotation of said planar wedge until said planar wedge enters said facet joint; sliding a substantially hollow drill guide over said spatula wherein said drill guide comprises a proximal end, a distal end, and a handle wherein said handle is nearer to the proximal end of said drill guide than to said distal end and wherein said distal end comprises opposed teeth; removing said spinal pin and said spatula from within said drill guide; inserting a drill bit into said drill guide; drilling a hole into a bone of said facet joint; removing said drill bit; sliding an inserter instrument into said drill guide wherein said inserter instrument has a proximal end and a distal end, wherein a facet joint bone plug is associated with said distal end and wherein said proximal end comprises a raised portion that prevents over-insertion of said facet joint bone plug;

disengaging the facet joint bone plug from said distal end of said inserter instrument into said drilled hole; and removing said drill guide.

15. A method according to claim 14 further comprising confirming the location of said spinal pin at said facet joint.

16. A method according to claim 15 wherein said confirming is accomplished with at least one x-ray.

17. A method according to claim 14 further comprising tapping said spatula further into said facet joint following the initial entry of said planar wedge into said facet joint.

18. A method according to claim 14 further comprising tapping said drill guide so that said opposed teeth of said drill guide engage facet joint bone to secure the orientation of said drill guide until said removing of said drill guide.

19. A method according to claim 14 further comprising tapping said facet joint bone plug into said hole following said facet joint bone plug's disengagement from said inserter instrument.

20. A method according to claim 14 wherein said spatula and said drill guide each further comprises a marking, wherein when said marking on said drill guide is matched or aligned with said marking on said spatula, the orientation of said opposed teeth is in approximately the same plane defined by said planar wedge.

21. A method according to claim 20 further comprising the step of matching or aligning said markings on said spatula and said drill guide.

22. A method according to claim 14 wherein said distal end of said drill guide comprises two opposed teeth.

23. A method according to claim 14 wherein said distal end of said drill guide comprises a plurality of teeth, wherein said plurality of teeth comprises two opposed teeth and one or more smaller teeth disposed between said two opposed teeth.

24. A method according to claim 14 wherein said drilling comprises grinding the bone and compacting some of the drilled bone within said hole.

* * * * *